United States Patent
Jha

(10) Patent No.: US 12,268,786 B2
(45) Date of Patent: *Apr. 8, 2025

(54) METHODS OF IMPROVING THE SOLUBILITY AND BIOAVAILABILITY OF THERAPEUTIC AGENTS

(71) Applicant: MAA Laboratories, Inc., Durham, NC (US)

(72) Inventor: Anjani Kumar Jha, Cary, NC (US)

(73) Assignee: MAA Laboratories, Inc., Durham, NC (US)

( * ) Notice: Subject to any disclaimer, the term of this patent is extended or adjusted under 35 U.S.C. 154(b) by 111 days.

This patent is subject to a terminal disclaimer.

(21) Appl. No.: 17/727,993

(22) Filed: Apr. 25, 2022

(65) Prior Publication Data

US 2023/0084932 A1 Mar. 16, 2023

Related U.S. Application Data

(63) Continuation of application No. 16/603,420, filed as application No. PCT/US2018/026522 on Apr. 6, 2018, now Pat. No. 11,311,493.

(60) Provisional application No. 62/482,944, filed on Apr. 7, 2017.

(51) Int. Cl.
| | |
|---|---|
| *A61K 9/51* | (2006.01) |
| *A61K 31/196* | (2006.01) |
| *A61K 31/4535* | (2006.01) |
| *A61K 31/58* | (2006.01) |
| *B02C 15/00* | (2006.01) |

(52) U.S. Cl.
CPC .......... *A61K 9/5192* (2013.01); *A61K 9/5138* (2013.01); *A61K 31/196* (2013.01); *A61K 31/4535* (2013.01); *A61K 31/58* (2013.01); *B02C 15/00* (2013.01); *Y10S 977/773* (2013.01); *Y10S 977/906* (2013.01)

(58) Field of Classification Search
CPC .............................. A61K 9/5192; B02C 15/00
See application file for complete search history.

(56) References Cited

U.S. PATENT DOCUMENTS

| | | |
|---|---|---|
| 6,984,404 B1 | 1/2006 | Talton et al. |
| 7,491,407 B2 | 2/2009 | Pourdeyhimi et al. |
| 11,311,493 B2 | 4/2022 | Jha |

(Continued)

FOREIGN PATENT DOCUMENTS

| | | |
|---|---|---|
| CN | 101365449 | 2/2009 |
| CN | 102438610 | 5/2012 |

(Continued)

OTHER PUBLICATIONS

Hosun Lim. "A Review of Soun Bond Processes." Journal of Textile and Apparel Technology and Management, vol. 6, Issue 3, Spring 2010, pp. 1-13. (Year: 2010).*

(Continued)

*Primary Examiner* — Isaac Shomer
(74) *Attorney, Agent, or Firm* — Fish & Richardson P.C.

(57) ABSTRACT

This invention relates to methods of preparing nanotherapeutic compounds and compositions comprising nanotherapeutic compounds. The nanotherapeutic compounds prepared according to the methods provided herein are useful for the treatment of disease, for example, cancer, in a subject in need thereof.

13 Claims, 16 Drawing Sheets

(56) References Cited

U.S. PATENT DOCUMENTS

| | | | |
|---|---|---|---|
| 2006/0159628 | A1 | 7/2006 | Liversidge et al. |
| 2007/0099996 | A1 | 5/2007 | Isloor |
| 2007/0148211 | A1* | 6/2007 | Altreuter .............. A61K 9/0095 |
| | | | 424/464 |
| 2010/0003319 | A1* | 1/2010 | Mehta ................ A61K 31/4535 |
| | | | 514/324 |
| 2010/0092563 | A1* | 4/2010 | Raffaele .................. A61P 35/00 |
| | | | 514/567 |
| 2012/0135047 | A1 | 5/2012 | Dodd et al. |
| 2014/0287039 | A1 | 9/2014 | Bosch et al. |
| 2015/0190402 | A1 | 7/2015 | Harmon et al. |
| 2016/0067265 | A1 | 3/2016 | Bosch et al. |
| 2016/0228573 | A1* | 8/2016 | Niyikiza ................ A61P 35/00 |

FOREIGN PATENT DOCUMENTS

| | | |
|---|---|---|
| CN | 103209687 | 7/2013 |
| WO | WO 2010/022193 | 2/2010 |
| WO | WO 2016/044701 | 3/2016 |

OTHER PUBLICATIONS

Garg et al., "Solid State Interaction of Raloxifene HCl with Different Hydrophilic Carriers During Co-grinding and its Effect on Dissolution Rate," Drug Development and Industrial Pharmacy, Apr. 2009, 35(4):455-470, 2 pages (Abstract).

Tian et al., "Using Flory-Huggins phase diagrams as a preformulation tool for the production of amorphous solid dispersions: a comparison between hot-melt extrusion and spray drying," Journal of Pharmacy and Pharmacology, Feb. 2014, 66(2):256-274.

Li et al., "Improving the API dissolution rate during pharmaceutical hot-melt extrusion I: Effect of the API particle size, and the co-rotating, twin-screw extruder screw configuration on the API dissolution rate," International Journal of Pharmaceutics, Jan. 2015, 478(1):103-112.

Alam et al., "Solid dispersions: a strategy for poorly aqueous soluble drugs and technology updates," Expert Opinion on Drug Delivery, Nov. 2012, 9(11):1419-1440.

Amanda J. Rogers, Amir Hashemi and Marianthi G. Ierapetritou. "Modeling of Particulate Processes for the Continuous Manufacture of Solid-Based Pharmaceutical Dosage Forms." Processes 2013, 1,67-127; doi:10.3390/pr1020067. (Year: 2013).

Andrews et al., "Physicochemical Characterization of Hot Melt Extruded Bicalutamide-Polyvinylpyrrolidone Solid Dispersions." Journal of Pharmaceutical Sciences, vol. 99, No. 3, Mar. 2010, pp. 1322-1335. (Year: 2010).

Crowley et al., "Pharmaceutical Applications of Hot-Melt Extrusion: Part I." Drug Development and Industrial Pharmacy, vol. 33, 2007, pp. 909-926. (Year: 2007).

Dorothea Sauer, Weijia Zheng, Lonique B. Coots, James W. McGinity. "Influence of processing parameters and formulation factors on the drug release from tablets powder-coated with Eudragit L 100-55." European Journal of Pharmaceutics and Biopharmaceutics, vol. 67 (2007) 464-475. (Year: 2007).

EP Extended European Search Report in European Appln. No. 18780455.4, dated Dec. 9, 2020, 10 pages.

Handbook of Pharmaceutical Excipients, 6th Edition, Rowe et al. (ed)., Feb. 2009, 196-198.

Handbook of Pharmaceutical Excipients, 6th Edition, Rowe et al. (ed)., Feb. 2009, 581-585.

Hosun Lim. "A Review of Spun Bond Processes." Journal of Textile and Apparel Technology and Management, vol. 6, Issue 3, Spring 2010, pp. 1-13. (Year: 2010).

International Search Report and Written Opinion for International Application No. PCT/US2018/026522 issued Jul. 11, 2018.

Michael A Repka, Soumyajit Majumdar, Sunil Kumar Battu, Ramesh Srirangam, Sampada B Upadhye. "Applications of hot-melt extrusion for drug delivery." Expert Opinion in Drug Delivery, vol. 5(12), 2008, pp. 1357-1376. (Year: 2008).

National Science Foundation, "National Science Foundation Award Abstract #1720591," https://www.nsf.gov/awardsearch/showAward?AWD_ID=1720591&HistoricalAwards=false accessed Oct. 5, 2020, published Jun. 9, 2017, 2 printed pages. (Year: 2017).

PCT International Preliminary Report on Patentability in International Appln. No. PCT/US2018/026522, mailed Oct. 17, 2019, 6 pages.

W. Zheng, M. Cerea, D. Sauer, J.W. McGinity. "Properties of theophylline tablets powder-coated with methacrylate ester copolymers." Journal of Drug Delivery Science and Technology, vol. 14 (4), 2004, pp. 319-325. (Year: 2004).

\* cited by examiner

METHODS OF IMPROVING THE SOLUBILITY AND BIOAVAILABILITY OF THERAPEUTIC AGENTS

CROSS-REFERENCE TO RELATED APPLICATIONS

This application is a continuation of U.S. application Ser. No. 16/603,420, filed Oct. 7, 2019, which is a U.S. National Stage Application under 35 U.S.C. § 371 of PCT/US2018/026522, filed Apr. 6, 2018, which claims the benefit of U.S. Provisional Application Ser. No. 62/482,944, filed Apr. 7, 2017, the disclosure of which is incorporated herein by reference in its entirety.

TECHNICAL FIELD

This invention relates to methods of preparing nanotherapeutic compounds and compositions comprising nanotherapeutic compounds which are useful for the treatment of disease. This technology may have additional applications, for example, in veterinary medicines and agricultural chemical application such herbicides and/or pesticides.

BACKGROUND

Improving bioavailability of a drug may lead to benefits in the treatment of various diseases in patients. Factors affecting bioavailability of an active agent may include, for example, the form of the dosage, mode of administration, and/or the solubility of the active agent.

SUMMARY

The present application provides, inter alia, a process comprising:
  i) milling a pharmaceutical composition in a ball milling apparatus to produce a nanoparticle form of the pharmaceutical composition; and
  ii) coating the nanoparticle form of the pharmaceutical composition with one or more polymers;
  wherein the pharmaceutical composition comprises a therapeutic agent, or a pharmaceutically acceptable salt thereof, and one or more pharmaceutically acceptable excipients.

In some embodiments, the nanoparticle form of the pharmaceutical composition comprises a nanoparticle form of the therapeutic agent. In some embodiments, the pharmaceutical composition comprises a solid mixture of the therapeutic agent and one or more pharmaceutically acceptable excipients.

In some embodiments, the milling of step i) comprises physically blending the pharmaceutical composition. In some embodiments, the milling of step i) is performed in the absence of a solvent component.

In some embodiments, prior to the milling of step i), the median particle size of the pharmaceutical composition is from about 1 to about 100 µm. It is understood that if the median particle size of the pharmaceutical composition is larger than about 100 µm, then additional size reduction techniques may be used to reduce the median particle size prior to performing the milling processes provided herein. In some embodiments, the processes provided herein further comprise milling a pharmaceutical composition having a median particle size which is larger than about 100 µm using a milling technique to form a pharmaceutical composition having a median particle size of from about 1 to about 100 µm.

In some embodiments, prior to the milling of step i), the median particle size of the pharmaceutical composition is from about 1 to about 75 µm. In some embodiments, prior to the milling of step i), the median particle size of the pharmaceutical composition is from about 1 to about 50 µm.

In some embodiments, the median particle size of the pharmaceutical composition is determined by laser diffraction, dynamic light scattering, or a combination thereof.

In some embodiments, the nanoparticle form of the pharmaceutical composition comprises a surface area which is about 2 to about 400 times greater than the surface area of the nanoparticle form of the pharmaceutical composition. In some embodiments, the nanoparticle form of the pharmaceutical composition comprises a surface area which is about 10 to about 300 times greater than the surface area of the pharmaceutical composition. In some embodiments, the nanoparticle form of the pharmaceutical composition comprises a surface area which is about 20 to about 200 times greater than the surface area of the pharmaceutical composition.

In some embodiments, the surface area of the nanoparticle form of the pharmaceutical composition is determined by laser diffraction.

In some embodiments, the bioavailability of the nanoparticle form of the therapeutic agent, or a pharmaceutically acceptable salt thereof, is increased by about 2 fold to about 20 fold.

In some embodiments, the solubility of the nanoparticle form of the therapeutic agent, or a pharmaceutically acceptable salt thereof, is increased by about 2 fold to about 50 fold compared to the therapeutic agent.

In some embodiments, the solubility of the nanoparticle form of the therapeutic agent, or a pharmaceutically acceptable salt thereof, is increased by about 2 fold to about 20 fold compared to the therapeutic agent. In some embodiments, the solubility of the nanoparticle form of the therapeutic agent, or a pharmaceutically acceptable salt thereof, is increased by about 2 fold to about 10 fold compared to the therapeutic agent.

In some embodiments, the pharmaceutical composition comprises about 1:100 stoichiometric ratio of therapeutic agent to the one or more pharmaceutically acceptable excipients. In some embodiments, the pharmaceutical composition comprises about a 1:50 stoichiometric ratio of therapeutic agent to the one or more pharmaceutically acceptable excipients. In some embodiments, the pharmaceutical composition comprises about a 1:10 stoichiometric ratio of therapeutic agent to the one or more pharmaceutically acceptable excipients.

In some embodiments, the pharmaceutical composition comprises from about 1 to about 20 pharmaceutically acceptable excipients. In some embodiments, the pharmaceutical composition comprises from about 1 to about 10 pharmaceutically acceptable excipients. In some embodiments, the pharmaceutical composition comprises from about 1 to about 5 pharmaceutically acceptable excipients.

In some embodiments, the coating of step ii) is performed using a melt extrusion process, a melt blown process, a Spunbond process, or a milling process (e.g., a high temperature milling process).

In some embodiments, each of the one of more polymers is independently selected from the group consisting of a carboxylic acid functionalized polymer, a neutral non-cellulosic polymer, and a cellulosic polymer. In some embodiments, the polymer is copovidone.

In some embodiments, the therapeutic agent is selected from the group consisting of a chemotherapeutic agent, an anti-inflammatory agent, an immunosuppressant, a steroid, an antibacterial agent, anti-parasitic agent, an anti-viral agent, an antimicrobial agent, and an antifungal agent. In some embodiments, the therapeutic agent is a chemotherapeutic agent. In some embodiments, the therapeutic agent is an anti-inflammatory agent. In some embodiments, the therapeutic agent is an immunosuppressant. In some embodiments, the therapeutic agent is a steroid. In some embodiments, the therapeutic agent is an antibacterial agent. In some embodiments, the therapeutic agent is an anti-parasitic agent. In some embodiments, the therapeutic agent is an anti-viral agent. In some embodiments, the therapeutic agent is an antimicrobial agent. In some embodiments, the therapeutic agent is an antifungal agent.

In some embodiments, the nanoparticle form of the therapeutic agent, or a pharmaceutically acceptable salt thereof, is crystalline, amorphous, or a combination thereof.

The present application further provides a compound, which is a nanoparticle form of a therapeutic agent provided herein, or a pharmaceutically acceptable salt thereof, wherein the nanoparticle form is prepared according to one or more of the processes provided herein.

In some embodiments, the compound is a nanoparticle form of a therapeutic agent selected from the group consisting of a chemotherapeutic agent, an anti-inflammatory agent, an immunosuppressant, a steroid, an antibacterial agent, anti-parasitic agent, an anti-viral agent, an antimicrobial agent, and an antifungal agent, or a pharmaceutically acceptable salt thereof.

In some embodiments, the compound is a nanoparticle form of a chemotherapeutic agent, or a pharmaceutically acceptable salt thereof.

In some embodiments, the compound is a nanoparticle form of a compound selected from the group consisting of raloxifene, dasatinib, abiraterone, sunitinib, axitinib, vandetanib, or cabozantinib, or a pharmaceutically acceptable salt thereof.

In some embodiments, the compound is a nanoparticle form of raloxifene, or a pharmaceutically acceptable salt thereof. In some embodiments, the compound is a nanoparticle form of raloxifene hydrochloride.

In some embodiments, the nanoparticle form of the raloxifene hydrochloride is characterized by a DSC thermogram having an endothermic peak at about 267° C.

In some embodiments, the nanoparticle form of the raloxifene hydrochloride has a DSC thermogram substantially as shown in FIG. 2.

In some embodiments, the nanoparticle form of the raloxifene hydrochloride is a crystalline form of raloxifene hydrochloride.

In some embodiments, the nanoparticle form of the raloxifene hydrochloride is an amorphous form of raloxifene hydrochloride.

In some embodiments, the nanoparticle form of the raloxifene hydrochloride is a combination of crystalline and amorphous forms of raloxifene hydrochloride.

In some embodiments, the nanoparticle form of the raloxifene hydrochloride has at least five XRD peaks, in terms of 2-theta, selected from about 12.5°, 16.2°, 19.5°, 19.6°, 19.0°, 20.8°, 21.0°, 23.0°, 25.5°, and 27.5°.

In some embodiments, the nanoparticle form of the raloxifene hydrochloride has at least four XRD peaks, in terms of 2-theta, selected from about 12.5°, 16.2°, 19.5°, 19.6°, 19.0°, 20.8°, 21.0°, 23.0°, 25.5°, and 27.5°.

In some embodiments, the nanoparticle form of the raloxifene hydrochloride has at least three XRD peaks, in terms of 2-theta, selected from about 12.5°, 16.2°, 19.5°, 19.6°, 19.0°, 20.8°, 21.0°, 23.0°, 25.5°, and 27.5°.

In some embodiments, the nanoparticle form of the raloxifene hydrochloride has at least two XRD peaks, in terms of 2-theta, selected from about 12.5°, 16.2°, 19.5°, 19.6°, 19.0°, 20.8°, 21.0°, 23.0°, 25.5°, and 27.5°.

In some embodiments, the nanoparticle form of the raloxifene hydrochloride has at least one XRD peak, in terms of 2-theta, selected from about 12.5°, 16.2°, 19.5°, 19.6°, 19.0°, 20.8°, 21.0°, 23.0°, 25.5°, and 27.5°.

In some embodiments, the nanoparticle form of the raloxifene hydrochloride has an XRD profile substantially as shown in FIG. 5.

In some embodiments, the nanoparticle form of the raloxifene hydrochloride has an FTIR profile substantially as shown in FIG. 3.

In some embodiments, the compound is a nanoparticle form of an anti-inflammatory agent, or a pharmaceutically acceptable salt thereof.

In some embodiments, the compound is a nanoparticle form of an immunosuppressant, or a pharmaceutically acceptable salt thereof.

In some embodiments, the compound is a nanoparticle form of a steroid, or a pharmaceutically acceptable salt thereof.

In some embodiments, the compound is a nanoparticle form of an antibacterial agent, or a pharmaceutically acceptable salt thereof.

In some embodiments, the compound is a nanoparticle form of an anti-parasitic agent, or a pharmaceutically acceptable salt thereof.

In some embodiments, the compound is a nanoparticle form of an anti-viral agent, or a pharmaceutically acceptable salt thereof.

In some embodiments, the compound is a nanoparticle form of an antimicrobial agent, or a pharmaceutically acceptable salt thereof.

In some embodiments, the compound is a nanoparticle form of an antifungal agent, or a pharmaceutically acceptable salt thereof.

In some embodiments, the nanoparticle form of the therapeutic agent, or a pharmaceutically acceptable salt thereof, is crystalline.

The present application further provides a pharmaceutical composition comprising a compound provided herein, or a pharmaceutically acceptable salt thereof, and one or more pharmaceutically acceptable excipients.

In some embodiments, the pharmaceutical composition is a nanoparticle form of the pharmaceutical composition.

The present application further provides a nanoparticle form of a pharmaceutical composition prepared according to one or more of the processes provided herein.

The present application further provides a pharmaceutical composition comprising a nanoparticle form of raloxifene, or a pharmaceutically acceptable salt thereof, which is prepared according to one or more of the processes provided herein.

The present application further provides a pharmaceutical composition comprising a nanoparticle form of raloxifene hydrochloride which is prepared according to one or more of the process provided herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Milling Processes

Figure 1:
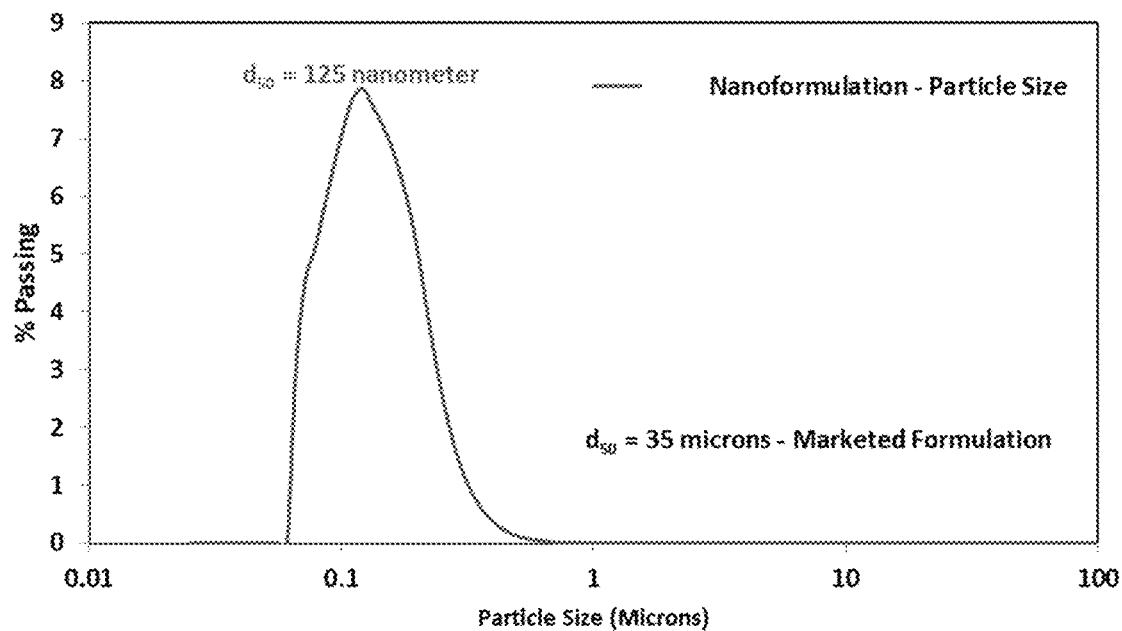
FIG. 1 shows particle size and distribution of a representative nanoformulation prepared according to a milling process provided herein.

The present application provides, inter alia, a process, comprising:
  i) milling a pharmaceutical composition or a therapeutic agent in a ball milling apparatus; and
  ii) coating the milled pharmaceutical composition or milled therapeutic agent with one or more polymers.

In some embodiments, the coating of step ii) stabilizes the pharmaceutical composition or therapeutic agent, enhances solubility of the pharmaceutical composition or therapeutic agent, enhances bioavailability of the pharmaceutical composition or therapeutic agent, enhances physicochemical characteristics of the pharmaceutical composition or therapeutic agent, enhances biological performance of the pharmaceutical composition or therapeutic agent, modulates the release profile of the pharmaceutical composition or therapeutic agent, or any combination thereof.

In some embodiments, the coating of step ii) improves the chemical stability of the milled pharmaceutical composition or therapeutic agent, increases the solubility of the milled pharmaceutical composition or therapeutic agent, increases the bioavailability of the milled pharmaceutical composition or therapeutic agent, improves the physicochemical characteristics of the milled pharmaceutical composition or therapeutic agent, improve the biological performance of the milled pharmaceutical composition or therapeutic agent, modulates the release profile of the milled pharmaceutical composition or therapeutic agent, or any combination or subcombination thereof.

In some embodiments, the coating of step ii) improves the chemical stability of the milled pharmaceutical composition (e.g., as compared to a milled pharmaceutical composition that has not been coated or a pharmaceutical composition that has not been milled according to step i). In some embodiments, the coating of step ii) improves the shelf life stability of the milled pharmaceutical composition or therapeutic agent. In some embodiments, the coating of step ii) improves the chemical stability of the milled pharmaceutical composition or therapeutic agent in a low pH environment (e.g., in the stomach of a subject).

In some embodiments, the coating of step ii) increases the solubility of the milled pharmaceutical composition (e.g., as compared to a milled pharmaceutical composition that has not been coated or a pharmaceutical composition that has not been milled according to step i).

In some embodiments, the coating of step ii) increases the bioavailability of the milled pharmaceutical composition (e.g., as compared to a milled pharmaceutical composition that has not been coated or a pharmaceutical composition that has not been milled according to step i).

In some embodiments, the coating of step ii) improves the physicochemical characteristics (e.g., solubility, pH profile, solid-state stability, solvent stability, and the like) of the milled pharmaceutical composition (e.g., as compared to a milled pharmaceutical composition that has not been coated or a pharmaceutical composition that has not been milled according to step i).

In some embodiments, the coating of step ii) modulates the biological performance (e.g., pharmacokinetic properties) of the milled pharmaceutical composition (e.g., as compared to a milled pharmaceutical composition that has not been coated or a pharmaceutical composition that has not been milled according to step i).

In some embodiments, the coating of step ii) modulates the release profile (e.g., controlled release, pulsatile release, sustained release, and the like) of the milled pharmaceutical composition (e.g., the release profile in a subject, as compared to a milled pharmaceutical composition that has not been coated or a pharmaceutical composition that has not been milled according to step i).

In some embodiments, the pharmaceutical composition comprises a therapeutic agent, or a pharmaceutically acceptable salt thereof, and one or more pharmaceutically acceptable excipients.

In some embodiments, the present application provides a process of preparing a nanoparticle form or a microparticle form of a pharmaceutical composition, or a nanoparticle form or a microparticle form of a therapeutic agent, comprising milling a pharmaceutical composition or a therapeutic agent in a ball milling apparatus (e.g., an attritor milling apparatus), thereby forming the nanoparticle form or microparticle form of the pharmaceutical composition, or the nanoparticle form or microparticle form of the therapeutic agent.

In some embodiments, the present application provides a process of coating a pharmaceutical composition or therapeutic agent (e.g., a nanoparticle form of a pharmaceutical composition or a nanoparticle form of a therapeutic agent) with one or more polymers.

In some embodiments, the process comprises:
  i) milling a pharmaceutical composition in a ball milling apparatus (e.g., an attritor milling apparatus) to produce a nanoparticle form of the pharmaceutical composition; and
  ii) coating the nanoparticle form of the pharmaceutical composition with one or more polymers;
  wherein the pharmaceutical composition comprises a therapeutic agent, or a pharmaceutically acceptable salt thereof, and one or more pharmaceutically acceptable excipients.

In some embodiments, the coating of step ii) stabilizes the pharmaceutical composition or therapeutic agent, enhances solubility of the pharmaceutical composition or therapeutic agent, enhances bioavailability of the pharmaceutical composition or therapeutic agent, enhances physicochemical characteristics of the pharmaceutical composition or therapeutic agent, enhances biological performance of the pharmaceutical composition or therapeutic agent, modulates the release profile of the pharmaceutical composition or therapeutic agent, or any combination thereof.

The processes provided herein provide nanoformulations which can contain a larger drug load (e.g., greater than 2% w/w) and provide methods of better controlling particle size of the nanoparticle forms compared to alternative processes available in the public domain. In some embodiments, the processes provide herein provide a nanoformulation containing a drug load of greater than about 2%, greater than about 10%, greater than about 25%, or greater than about 50% w/w. In some embodiments, the nanoformulation or microformulation comprises a drug load of from about 10% to about 20% w/w. In some embodiments, the nanoformulation or microformulation comprises a drug load of from about 10% w/w to about 15% w/w. In some embodiments, the nanoformulation or microformulation comprises a drug load of from about 15% w/w to about 20% w/w. In some embodiments, the nanoformulation or microformulation comprises a drug load of about 10% w/w. In some embodiments, the nanoformulation or microformulation comprises a drug load of about 12% w/w. In some embodiments, the nanoformulation or microformulation comprises a drug load of about 15% w/w. In some embodiments, the nanoformulation or microformulation comprises a drug load of about 20% w/w. The processes provided herein also comprise substantially fewer steps in preparing stable nanoparticles compared to alternative processes available in the public domain.

In some embodiments, the coating of step ii) is performed as a batch process. In some embodiments, the coating of step ii) is performed as a continuous process.

The coating of step ii) stabilizes the nanoparticles prepared in step i), thereby preventing or inhibiting aggregation, agglomeration, or a combination thereof, of the nanoparticles. In some embodiments, the coating of step ii) inhibits aggregation of the nanoparticles prepared in step i). In some embodiments, the coating of step ii) inhibits agglomeration of the nanoparticles prepared in step i). In some embodiments, the coating of step ii) prevents aggregation of the nanoparticles prepared in step i). In some embodiments, the coating of step ii) prevents agglomeration of the nanoparticles prepared in step i).

The coating of step ii) further enhances the permeability of the pharmaceutical composition or therapeutic agent. For example, the coating may increase the permeability of the pharmaceutical composition or therapeutic agent for use in technologies associated with therapeutic agents classified in the biopharmaceutics classification system (BCS) as BCS II, BCS III, and/or BCS IV agents.

The coating of step ii) also decreases the likelihood of drug-drug interactions of pharmaceutical compositions comprising more than one active pharmaceutical ingredient (API) and allows for the preparation of more than one drug in a unit dose.

In some embodiments, the processes provided herein provide a coated pharmaceutical composition (e.g., a coated nanoparticle form of a pharmaceutical composition) or a coated therapeutic agent wherein the nanoparticles are crystalline nanoparticles, amorphous nanoparticles, or a combination thereof. In some embodiments, the nanoparticles crystalline nanoparticles. In some embodiments, the nanoparticles are amorphous nanoparticles. In some embodiments, the nanoparticles comprise a mixture of crystalline and amorphous nanoparticles.

In some embodiments, the nanoparticle form of the pharmaceutical composition comprises a nanoparticle form of the therapeutic agent. In some embodiments, the pharmaceutical composition comprises a solid mixture of the therapeutic agent and one or more pharmaceutically acceptable excipients.

In some embodiments, the milling of step i) comprises physically blending the pharmaceutical composition. In some embodiments, the milling of step i) is performed in the absence of a solvent component.

In some embodiments, the milling is performed using steel balls, zirconia balls, glass beads, or any combination thereof. In some embodiments, the milling is performed using balls and/or beads having an average diameter of about 0.1 inch to about 0.5 inches, for example, about 0.1 inch to about 0.5 inches, about 0.1 inch to about 0.4 inches, about 0.1 inch to about 0.3 inches, about 0.1 inch to about 0.25 inches, about 0.1 inch to about 0.2 inches, about 0.2 inches to about 0.5 inches, about 0.2 inches to about 0.4 inches, about 0.2 inches to about 0.3 inches, about 0.2 inches to about 0.25 inches, about 0.25 inches to about 0.5 inches, about 0.25 inches to about 0.4 inches, about 0.25 inches to about 0.3 inches, about 0.3 inches to about 0.5 inches, about 0.3 inches to about 0.4 inches, or about 0.4 inches to about 0.5 inches. In some embodiments, the milling is performed using balls and/or beads having an average diameter of about 0.2 inches to about 0.4 inches. In some embodiments, the milling is performed using balls and/or beads having an average diameter of about 0.25 inches to about 0.375 inches (i.e., ¼" to about ⅜"). In some embodiments, the milling is performed using balls and/or beads having an average diameter of about 0.25 inches (i.e. ¼"). In some embodiments, the milling is performed using balls and/or beads having an average diameter of about 0.375 inches (i.e. ⅜"). In some embodiments, the ball milling apparatus is an attritor mill.

In some embodiments, prior to the milling of step i), the median particle size of the pharmaceutical composition is from about 1 μm to about 100 μm, for example, from about 1 μm to about 100 μm, from about 1 μm to about 90 μm, from about 1 μm to about 80 μm, from about 1 μm to about 70 μm, from about 1 μm to about 60 μm, from about 1 μm to about 50 μm, from about 1 μm to about 40 μm, from about 1 μm to about 30 μm, from about 1 μm to about 20 μm, from about 1 μm to about 10 μm, from about 10 μm to about 100 μm, from about 10 μm to about 90 μm, from about 10 μm to about 80 μm, from about 10 μm to about 70 μm, from about 10 μm to about 60 μm, from about 10 μm to about 50 μm, from about 10 μm to about 40 μm, from about 10 μm to about 30 μm, from about 10 μm to about 20 μm, from about 20 μm to about 100 μm, from about 20 μm to about 90 μm, from about 20 μm to about 80 μm, from about 20 μm to about 70 μm, from about 20 μm to about 60 μm, from about 20 μm to about 50 μm, from about 20 μm to about 40 μm, from about 20 μm to about 30 μm, from about 30 μm to about 100 μm, from about 30 μm to about 90 μm, from about 30 μm to about 80 μm, from about 30 μm to about 70 μm, from about 30 μm to about 60 μm, from about 30 μm to about 50 μm, from about 30 μm to about 40 μm, from about 40 μm to about 100 μm, from about 40 μm to about 90 μm, from about 40 μm to about 80 μm, from about 40 μm to about 70 μm, from about 40 μm to about 60 μm, from about 40 μm to about 50 μm, from about 50 μm to about 100 μm, from about 50 μm to about 90 μm, from about 50 μm to about 80 μm, from about 50 μm to about 70 μm, from about 50 μm to about 60 μm, from about 60 μm to about 100 μm, from about 60 μm to about 90 μm, from about 60 μm to about 80 μm, from about 60 μm to about 70 μm, from about 70 μm to about 100 μm, from about 70 μm to about 90 μm, from about 70 μm to about 80 μm, from about 80 μm to about 100 μm, from about 80 μm to about 90 μm, or from about 90 μm to about 100 μm. In some embodiments, prior to the milling of step i), the median particle size of the pharmaceutical composition is from about 1 to about 80 μm. In some embodiments, prior to the milling of step i), the median particle size of the pharmaceutical composition is from about 1 to about 75 μm. In some embodiments, prior to the milling of step i), the median particle size of the pharmaceutical composition is from about 1 to about 50 μm.

In some embodiments, the median particle size of the pharmaceutical composition may be determined by processes which are standard in the field and readily known to one of ordinary skill in the art (e.g., laser diffraction and/or dynamic light scattering). In some embodiments, the median particle size of the pharmaceutical composition is determined by laser diffraction, dynamic light scattering, or a combination thereof.

In some embodiments, the nanoparticle form of the pharmaceutical composition comprises a surface area which is about 2 to about 400 times greater than the surface area of the nanoparticle form of the pharmaceutical composition, for example, about 2 to about 400 times greater, about 2 to about 300 times greater, about 2 to about 200 times greater, about 2 to about 100 times greater, about 2 to about 50 times greater, about 2 to about 10 times greater, about 10 to about 400 times greater, about 10 to about 300 times greater, about 10 to about 200 times greater, about 10 to about 100 times greater, about 10 to about 50 times greater, about 50 to about 400 times greater, about 50 to about 300 times greater, about 50 to about 200 times greater, about 50 to about 100 times greater, about 100 to about 400 times greater, about 100 to about 300 times greater, about 100 to about 200 times greater, about 200 to about 400 times greater, about 200 to about 300 times greater, or about 300 to about 400 times greater. In some embodiments, the nanoparticle form of the pharmaceutical composition comprises a surface area which is about 10 to about 300 times greater than the surface area of the pharmaceutical composition. In some embodiments, the nanoparticle form of the pharmaceutical composition comprises a surface area which is about 20 to about 200 times greater than the surface area of the pharmaceutical composition.

In some embodiments, the surface area of the nanoparticle form of the pharmaceutical composition may be determined by processes which are standard in the field and readily known to one of ordinary skill in the art (e.g., laser diffraction). In some embodiments, the surface area of the nanoparticle form of the pharmaceutical composition is determined by laser diffraction.

In some embodiments, the bioavailability of the nanoparticle form of the therapeutic agent, or a pharmaceutically acceptable salt thereof, prepared according to the methods provided herein is increased compared to a non-nanoparticle form of the therapeutic agent, or a pharmaceutically acceptable salt thereof (i.e., the therapeutic agent, or a pharmaceutically acceptable salt thereof, prior to performing the methods described herein).

In some embodiments, the bioavailability of the nanoparticle form of the therapeutic agent, or a pharmaceutically acceptable salt thereof, prepared according to the methods provided herein is increased by about 2 fold to about 20 fold compared to a non-nanoparticle form of the therapeutic agent, or a pharmaceutically acceptable salt thereof, for example, about 2 fold to about 20 fold, about 2 fold to about 15 fold, about 2 fold to about 10 fold, about 2 fold to about 5 fold, about 5 fold to about 20 fold, about 5 fold to about 15 fold, about 5 fold to about 10 fold, about 10 fold to about 20 fold, about 10 fold to about 15 fold, or about 15 fold to about 20 fold.

In some embodiments, the solubility of the nanoparticle form of the therapeutic agent, or a pharmaceutically acceptable salt thereof, prepared according to the methods provided herein is increased compared to a non-nanoparticle form of the therapeutic agent, or a pharmaceutically acceptable salt thereof (i.e., the therapeutic agent, or a pharmaceutically acceptable salt thereof, prior to performing the methods described herein).

In some embodiments, the solubility of the nanoparticle form of the therapeutic agent, or a pharmaceutically acceptable salt thereof, prepared according to the methods provided herein is increased by about 2 fold to about 100 fold compared to a non-nanoparticle form of the therapeutic agent, or a pharmaceutically acceptable salt thereof, for example, about 2 fold to about 100 fold, about 2 fold to about 50 fold, about 2 fold to about 20 fold, about 2 fold to about 10 fold, about 2 fold to about 5 fold, about 5 fold to about 100 fold, about 5 fold to about 50 fold, about 5 fold to about 20 fold, about 5 fold to about 10 fold, about 10 fold to about 100 fold, about 10 fold to about 50 fold, about 10 fold to about 20 fold, about 20 fold to about 100 fold, about 20 fold to about 50 fold, or about 50 fold to about 100 fold. In some embodiments, the solubility of the nanoparticle form of the therapeutic agent, or a pharmaceutically acceptable salt thereof, is increased by about 2 fold to about 20 fold compared to the therapeutic agent. In some embodiments, the solubility of the nanoparticle form of the therapeutic agent, or a pharmaceutically acceptable salt thereof, is increased by about 2 fold to about 50 fold compared to the therapeutic agent.

In some embodiments, the pharmaceutical composition comprises about 1:100 stoichiometric ratio of therapeutic agent to the one or more pharmaceutically acceptable excipients (i.e., therapeutic agent:one or more pharmaceutically acceptable excipient), for example, about 1:100, about 1:90, about 1:80, about 1:70, about 1:60, about 1:50, about 1:40, about 1:30, about 1:20, about 1:10, about 1:5, or about 1:2. In some embodiments, the pharmaceutical composition comprises about 1:50 stoichiometric ratio of therapeutic agent to the one or more pharmaceutically acceptable excipients. In some embodiments, the pharmaceutical composition comprises about 1:10 stoichiometric ratio of therapeutic agent to the one or more pharmaceutically acceptable excipients.

In some embodiments, the pharmaceutical composition comprises from about 1 to about 20 pharmaceutically acceptable excipients, for example, about 1 to about 20, about 1 to about 15, about 1 to about 10, about 1 to about 5, about 1 to about 3, about 1 to about 2, about 2 to about 20, about 2 to about 15, about 2 to about 10, about 2 to about 5, about 2 to about 3, about 3 to about 20, about 3 to about 15, about 3 to about 10, about 3 to about 5, about 5 to about 20, about 5 to about 15, about 5 to about 10, about 10 to about 20, about 10 to about 15, or about 15 to about 20. In some embodiments, the pharmaceutical composition comprises from about 1 to about 10 pharmaceutically acceptable excipients. In some embodiments, the pharmaceutical composition comprises from about 1 to about 5 pharmaceutically acceptable excipients.

In some embodiments, the coating of step ii) is performed according to one or more processes described in U.S. Pat. No. 7,491,407, the disclosure of which is incorporated herein by reference in its entirety. For example, the coating of step ii) may comprise the following steps:
(1) a preparation step, wherein the ingredients of the micron size particles (i.e., microparticle) or nanoparticle form of the pharmaceutical composition are mixed and melted or softened;
(2) an extrusion step and, optionally,
a (3) cooling and/or shaping step.

Figure 2:
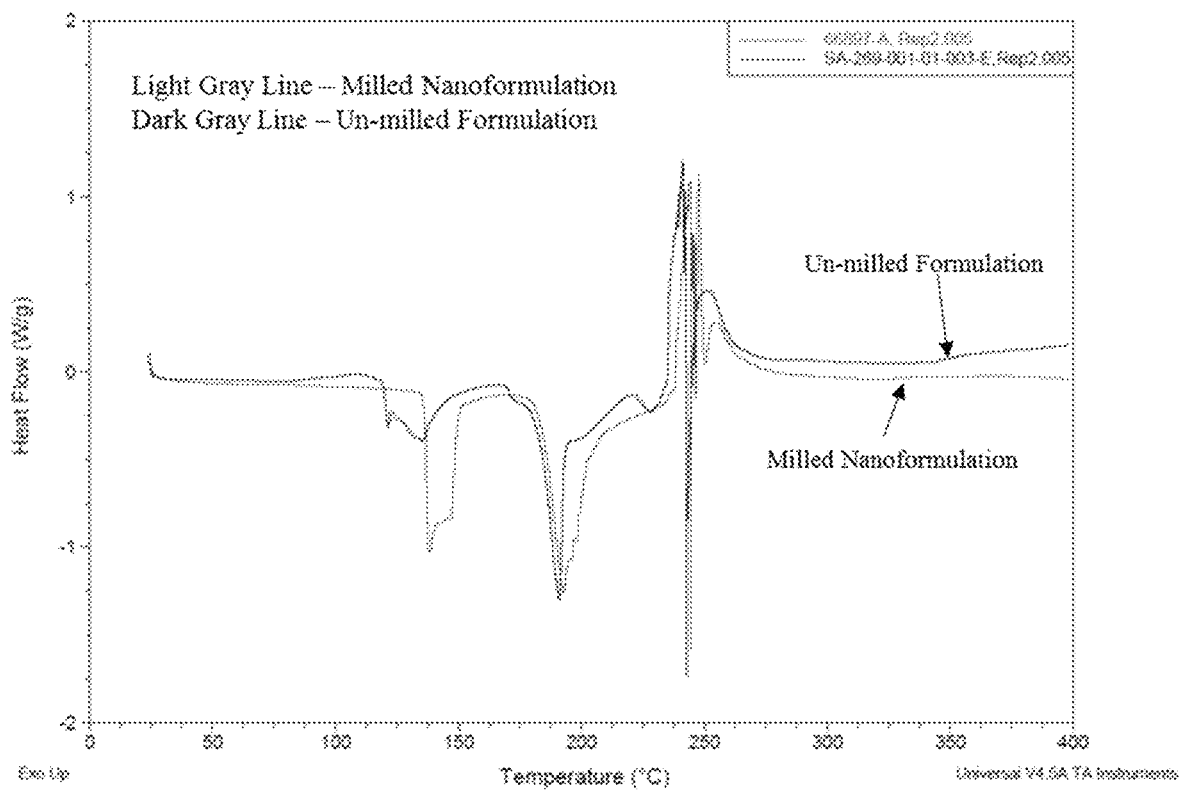
FIG. 2 shows a comparison of Differential Scanning calorimetry (DSC) thermograms for a representative milled nanoformulation and an un-milled formulation.

Example extrusion processes useful in the coating of step ii) are shown, for example, in FIGS. 1-2 of U.S. Pat. No. 7,491,407.

In some embodiments, the coating of step ii) is performed using a melt extrusion process, a melt blown process, or a Spunbond process, or milling of polymer with other excipients and drugs at high temperature. In some embodiments, the coating of step ii) is performed using a melt extrusion process.

In some embodiments, the nanoparticle form of the pharmaceutical composition prepared according to the methods provided herein is in the form of one or more fibers which have enhanced surface areas in order to accommodate and facilitate faster dissolution of the drug and other agents (e.g., polymer coating).

In some embodiments, the coating of step ii) can be applied to achieve localized drug delivery.

In some embodiments, the coating of step ii) can be applied to minimize and/or prevent adverse effects associated with the therapeutic agent or pharmaceutical composition, toxicity associated with the therapeutic agent or pharmaceutical composition, or any combination thereof.

In some embodiments, the coating of step ii) is applied to form an immediate release composition, a controlled release composition, a sustained release composition, a fast melt composition, a pulsatile release composition, a mixed immediate release profile, and/or any combination release profile.

In some embodiments, the polymer coating can be applied as a thin coating (e.g., <400 nm thickness). In some embodiments, the polymer coating can be applied as a thick coating (e.g., >400 nm).

In some embodiments, the coating of step ii) comprises coating the nanoparticle form of the pharmaceutical composition with one or more polymers in a suitable polymer carrier by compounding and/or blending, extruding the blended or compounded material by extruding, thereby providing means for the delivery of the polymer-coated nanoparticle composition. Examples of fibers that can be prepared according to the coating processes described herein are shown, for example, in FIGS. 5-13 of U.S. Pat. No. 7,491,407. In some embodiments, the fibers are hollow. In some embodiments, the fibers comprise a sheath cross section, a core cross-section, a solid cross section, or a hollow cross-section. In some embodiments, the fibers are formed into a ribbon or stacked configuration. In some embodiments, the fibers comprise a side by side cross section. In some embodiments, the fibers comprise an island in the sea cross-section. In some embodiments, the fibers comprise a segmented pie cross section. In some embodiments, the polymer is a fiber or non-fibrous polymer.

In some embodiments, each of the one or more polymers used in the coating of step ii) is independently selected from the group consisting of a carboxylic acid functionalized polymer, a neutral non-cellulosic polymer, and a cellulosic polymer.

In some embodiments, the polymer used in the coating of step ii) comprises one or more neutral non-cellulosic polymers. Exemplary polymers include: vinyl polymers and copolymers having substituents that are hydroxy, alkyl, acyloxy, and cyclic amides. These include polyvinyl alcohols that have at least a portion of their repeat units in the unhydrolyzed (e.g., vinyl acetate) form (e.g., polyvinyl alcohol-polyvinyl acetate copolymers); polyvinyl pyrrolidinone; polyethylene polyvinyl alcohol copolymers; polyethylene polyvinyl alcohol, kollidon VA64, plasdone S630, polaxamer, polyvinylpyrrolidinone and polyvinylpyrrolidinonecopolymers, such as polyvinylpyrrolidinone-polyvinyl acetate copolymers and polyvinyl caprolactam-polyvinyl acetate-polyethylene glycol graft copolymer. In some embodiments, the polymer comprises copovidone. In some embodiments, the polymer is copovidone.

In some embodiments, the polymer used in the coating of step ii) comprises one or more carboxylic acid functionalized polymers. Examples of carboxylic acid functionalized polymers include, but are not limited to, carboxylic acid functionalized: vinyl polymers, polymethacrylates, polyacrylates, amine functionalized polyacrylates, proteins, and carboxylic acid functionalized starches such as starch glycolate.

In some embodiments, the polymer used in the coating of step ii) comprises one or more cellulosic polymers. Example cellulosic polymers include, but are not limited to, Cellulosic polymers with at least one ester- and/or ether-linked: ethylbenzoic acid cellulose, ethyoxybenzoic acid substituents, cellulose pthalate; hydroxypropyl methyl cellulosic acetate succinate, hydroxypropyl methyl cellulose phthalate, cellulose acetate phathalate, hydroxypropyl cellulose acetate phthalate, cellulose acetate terephthalate and cellulose acetate isophthalate. In some embodiments, the cellulosic polymer is at least partially ionizable at physiologically relevant pH and include at least one ionizable substituent, which may be either ether-linked or ester-linked.

In some embodiments, the polymers used in the coating of step ii) is copovidone.

It is understood that polymers which are suitable for in the compounds, compositions, and processes provided herein are blended, the blends of such polymers may also be useful in the present invention. Thus, it is understood that the term polymer is intended to include blends of polymers in addition to a single species of polymer. Additional polymers useful in the present invention also include one or more of the polymers disclosed in U.S. Application Publication No. 2015/0190402 (see e.g., [0014]-[0036]), the disclosure of which is incorporated herein by reference in its entirety.

In some embodiments, the nanoparticle form of the therapeutic agent, or a pharmaceutically acceptable salt thereof, is crystalline.

In some embodiments, the therapeutic agent is selected from the group consisting of a chemotherapeutic agent, an anti-inflammatory agent, an immunosuppressant, a steroid, an antibacterial agent, anti-parasitic agent, an anti-viral agent, an antimicrobial agent, and an antifungal agent.

In some embodiments, the therapeutic agent is a chemotherapeutic agent. In some embodiments, the therapeutic agent is an anti-inflammatory agent. In some embodiments, the therapeutic agent is an immunosuppressant. In some embodiments, the therapeutic agent is a steroid. In some embodiments, the therapeutic agent is an antibacterial agent. In some embodiments, the therapeutic agent is an anti-parasitic agent. In some embodiments, the therapeutic agent is an anti-viral agent. In some embodiments, the therapeutic agent is an antimicrobial agent. In some embodiments, the therapeutic agent is an antifungal agent.

Example therapeutic agents which may be used methods provided herein include, but are not limited to: raloxifene, a cytostatic agent, a proteosome inhibitor, cisplatin, doxorubicin, taxol, etoposide, irinotecan, topotecan, paclitaxel, docetaxel, epothilones, tamoxifen, 5-fluorouracil, temozolomide, tipifarnib, gefitinib, erlotinib hydrochloride, antibodies to EGFR, imatinib mesylate, gemcitabine, uracil mustard, chlormethine, ifosfamide, melphalan, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide, 17α-ethynylestradiol, diethylstilbestrol, testosterone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, rituximab, alemtuzumab, clofarabine, cladribine, aphidicolin, sunitinib, dasatinib, tezacitabine, triapine, didox, trimidox, amidox, bendamustine, ofatumumab, idelalisib, a corticosteroid such as cortisone, dexamethasone, hydrocortisone, methylprednisolone, prednisolone, or prednisone, an anti-histamines such as cetirizine, fexofenadine, hydroxyzine, loratadine, ephedrine, or theophylline, azathioprine, chlorambucil, cyclophosphamide, cyclosporine, daclizumab, infliximab, methotrexate, tacrolimus, an aminoglycoside such as gentamicin, neomycin, or streptomycin, a penicillin such as amoxicillin or ampicillin, a macrolide such as erythromycin, a polyene agent such as amphotericin B or candicidin, an imidazole agent such as bifonazole, clotrimazole, or econazole, a triazole agent such as albaconazole, efinaconazole, or fluconazole, a thiazole agent such as abafungin, an allylamine agent such as amorolfin, butenafine, or naftifine, an echinocandin such as anidulafungin or caspofungi, aspirin, a choline salicylate, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

In some embodiments, the therapeutic agent is selected from the group consisting of raloxifene, dasatinib, abiraterone, sunitinib, axitinib, vandetanib, or cabozantinib, or a pharmaceutically acceptable salt thereof. In some embodiments, the therapeutic agent is raloxifene, or a pharmaceutically acceptable salt thereof. In some embodiments, the therapeutic agent is raloxifene hydrochloride.

Nanoparticle Compounds and Pharmaceutical Compositions

The present application further provides a compound, which is a nanoparticle form of a therapeutic agent provided herein, or a pharmaceutically acceptable salt thereof, wherein the nanoparticle form is prepared according to one or more of the processes provided herein. In some embodiments, the nanoparticle form of the therapeutic agent, or a pharmaceutically acceptable salt thereof, is crystalline, amorphous, or a combination thereof.

The term "compound" as used herein is meant to include all stereoisomers, geometric isomers, tautomers, and isotopes of the species depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

In some embodiments, the compound is a nanoparticle form of a chemotherapeutic agent, or a pharmaceutically acceptable salt thereof. In some embodiments, the compound is a nanoparticle form of an anti-inflammatory agent, or a pharmaceutically acceptable salt thereof. In some embodiments, the compound is a nanoparticle form of an immunosuppressant, or a pharmaceutically acceptable salt thereof. In some embodiments, the compound is a nanoparticle form of a steroid, or a pharmaceutically acceptable salt thereof. In some embodiments, the compound is a nanoparticle form of an antibacterial agent, or a pharmaceutically acceptable salt thereof. In some embodiments, the compound is a nanoparticle form of an anti-parasitic agent, or a pharmaceutically acceptable salt thereof. In some embodiments, the compound is a nanoparticle form of an anti-viral agent, or a pharmaceutically acceptable salt thereof. In some embodiments, the compound is a nanoparticle form of an antimicrobial agent, or a pharmaceutically acceptable salt thereof. In some embodiments, the compound is a nanoparticle form of an antifungal agent, or a pharmaceutically acceptable salt thereof.

In some embodiments, the compound is a nanoparticle form of a compound selected from the group consisting of raloxifene, dasatinib, abiraterone, sunitinib, axitinib, vandetanib, or cabozantinib, or a pharmaceutically acceptable salt thereof.

In some embodiments, the compound is a nanoparticle form of raloxifene, or a pharmaceutically acceptable salt thereof. In some embodiments, the compound is a nanoparticle form of raloxifene hydrochloride. In some embodiments, the compound is a nanoparticle form of abiraterone. In some embodiments, the compound is a nanoparticle form of abiraterone acetate.

In some embodiments, the compound is a nanoparticle form of raloxifene, or a pharmaceutically acceptable salt thereof, which is crystalline. In some embodiments, the compound is a nanoparticle form of raloxifene hydrochloride, which is crystalline.

In some embodiments, the compound is a nanoparticle form of raloxifene, or a pharmaceutically acceptable salt thereof, which is amorphous. In some embodiments, the compound is a nanoparticle form of raloxifene hydrochloride, which is amorphous.

In some embodiments, the compound is a nanoparticle form of raloxifene, or a pharmaceutically acceptable salt thereof, which is crystalline, amorphous, or a combination thereof. In some embodiments, the compound is a nanoparticle form of raloxifene hydrochloride, which is crystalline, amorphous, or a combination thereof.

In some embodiments, the nanoparticle form of the raloxifene hydrochloride is characterized by a DSC thermogram having an endothermic peak at about 267° C. In some embodiments, the nanoparticle form of the raloxifene hydrochloride has a DSC thermogram substantially as shown in FIG. 2.

In some embodiments, the nanoparticle form of the raloxifene hydrochloride has at least seven XRD peaks, in terms of 2-theta, selected from about 12.5°, about 16.2°, about 19.5°, about 19.6°, about 19.0°, about 20.8°, about 21.0°, about 23.0°, about 25.5°, and about 27.5°.

In some embodiments, the nanoparticle form of the raloxifene hydrochloride has at least six XRD peaks, in terms of 2-theta, selected from about 12.5°, about 16.2°, about 19.5°, about 19.6°, about 19.0°, about 20.8°, about 21.0°, about 23.0°, about 25.5°, and about 27.5°.

In some embodiments, the nanoparticle form of the raloxifene hydrochloride has at least five XRD peaks, in terms of 2-theta, selected from about 12.5°, about 16.2°, about 19.5°, about 19.6°, about 19.0°, about 20.8°, about 21.0°, about 23.0°, about 25.5°, and about 27.5°.

In some embodiments, the nanoparticle form of the raloxifene hydrochloride has at least four XRD peaks, in terms of 2-theta, selected from about 12.5°, about 16.2°, about 19.5°, about 19.6°, about 19.0°, about 20.8°, about 21.0°, about 23.0°, about 25.5°, and about 27.5°.

In some embodiments, the nanoparticle form of the raloxifene hydrochloride has at least three XRD peaks, in terms of 2-theta, selected from about 12.5°, about 16.2°, about 19.5°, about 19.6°, about 19.0°, about 20.8°, about 21.0°, about 23.0°, about 25.5°, and about 27.5°.

In some embodiments, the nanoparticle form of the raloxifene hydrochloride has at least two XRD peaks, in terms of 2-theta, selected from about 12.5°, about 16.2°, about 19.5°, about 19.6°, about 19.0°, about 20.8°, about 21.0°, about 23.0°, about 25.5°, and about 27.5°.

In some embodiments, the nanoparticle form of the raloxifene hydrochloride has at least one XRD peaks, in terms of 2-theta, selected from about 12.5°, about 16.2°, about 19.5°, about 19.6°, about 19.0°, about 20.8°, about 21.0°, about 23.0°, about 25.5°, and about 27.5°.

Figure 5:
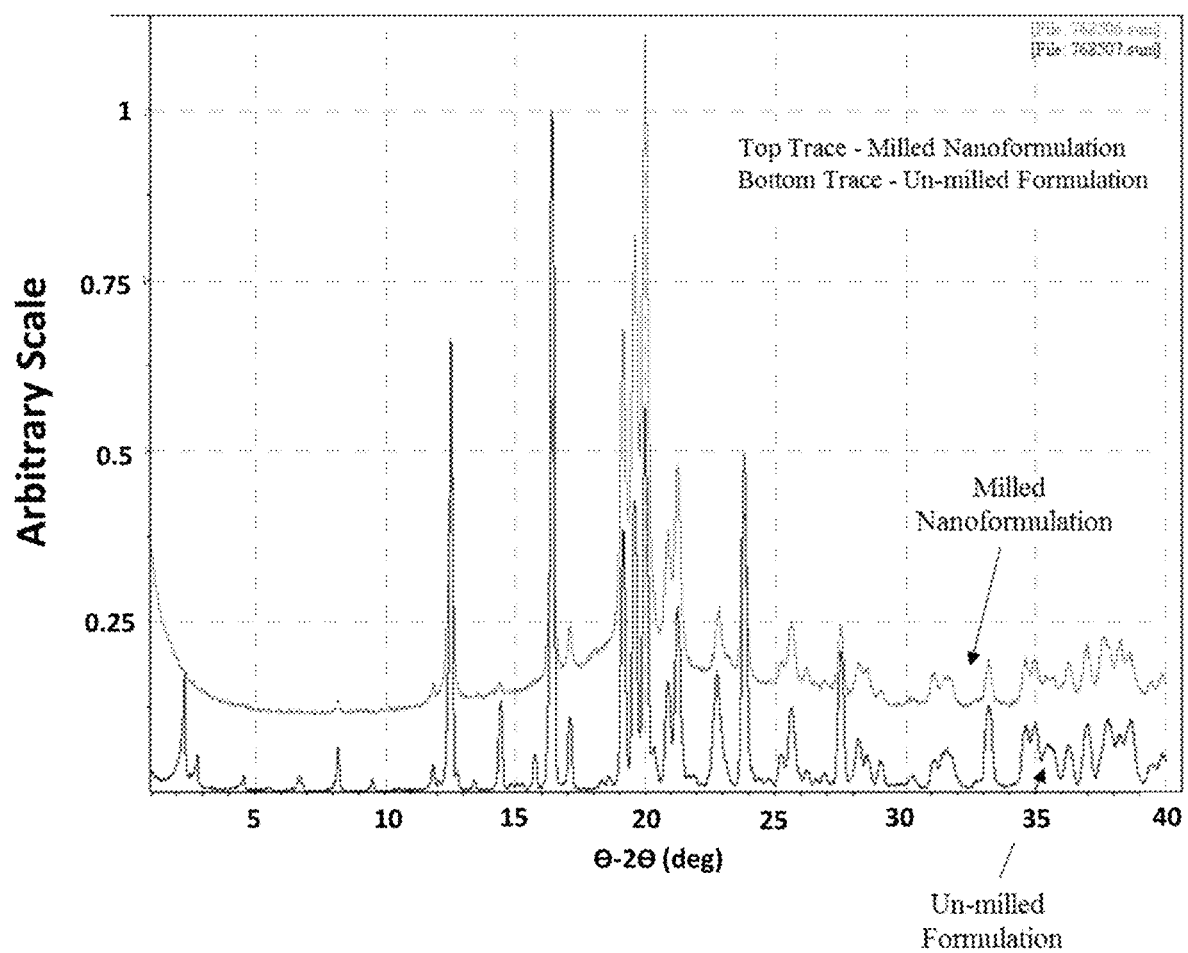
FIG. 5 shows a comparison of XRD spectra of a nanoformulation of raloxifene HCl prepared according to a milling process provided herein and an un-milled formulation.

In some embodiments, the nanoparticle form of the raloxifene hydrochloride has an XRD profile substantially as shown in FIG. 5.

Figure 3:
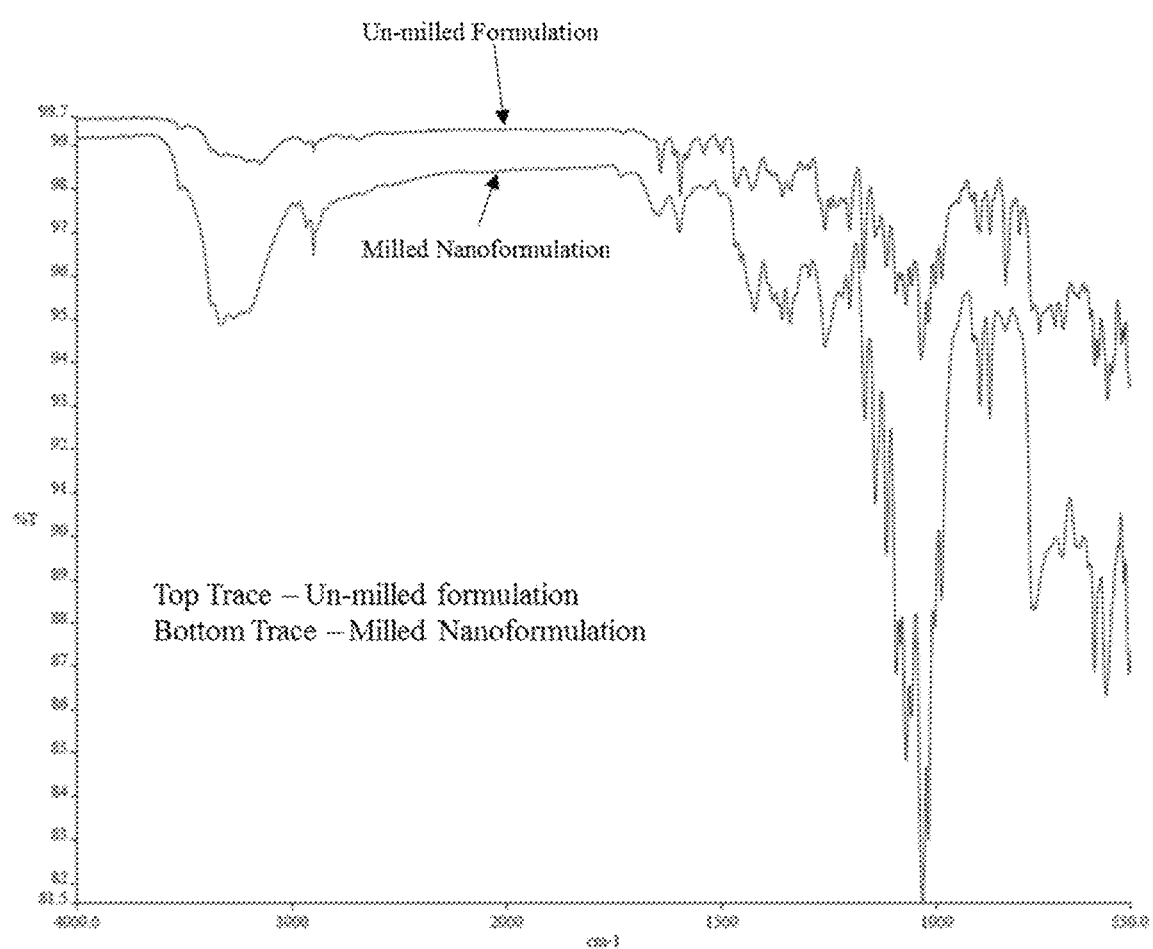
FIG. 3 shows a comparison of fourier transform infrared (FTIR) spectra of raloxifene HCl from a nanoformulation prepared according to a milling process provided herein and an un-milled formulation.

In some embodiments, the nanoparticle form of the raloxifene hydrochloride has an FTIR profile substantially as shown in FIG. 3.

In some embodiments, the compound is a nanoparticle form of diclofenac (i.e., 2-(2,6-dichloranilino)phenylacetic acid; diclofenac acid), or a pharmaceutically acceptable salt thereof.

In some embodiments, the compound is a nanoparticle form of diclofenac, or a pharmaceutically acceptable salt thereof, which is crystalline.

In some embodiments, the compound is a nanoparticle form of diclofenac, or a pharmaceutically acceptable salt thereof, which is amorphous.

In some embodiments, the compound is a nanoparticle form of diclofenac, or a pharmaceutically acceptable salt thereof, which is crystalline, amorphous, or a combination thereof.

Figure 17:
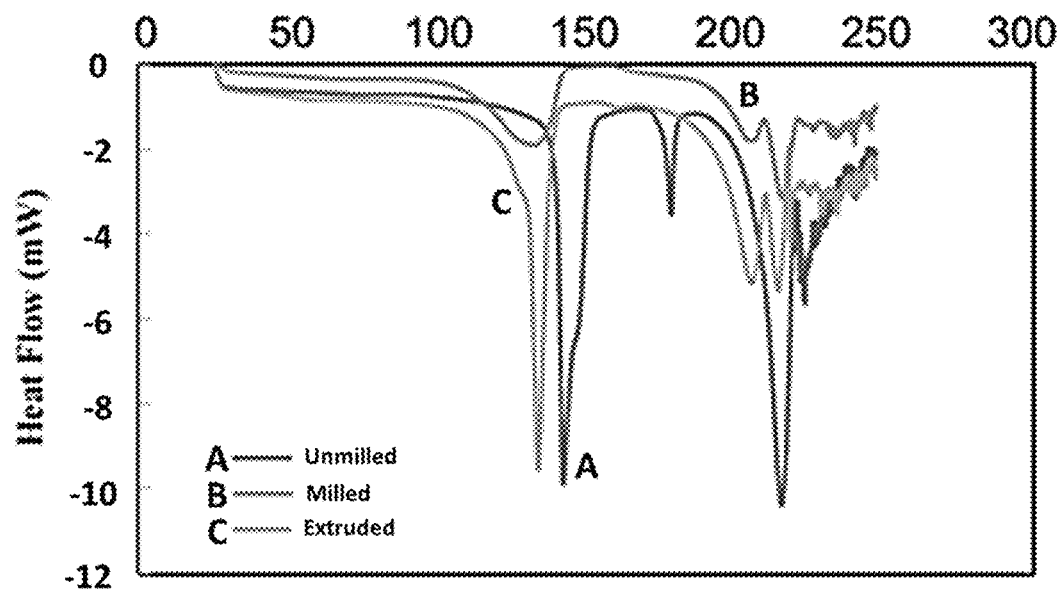
FIG. 17 shows differential scanning calorimetry data comparing the melting peaks of diclofenac acid before milling, after milling, and after extrusion. Similar peaks with different magnitude confirms that melting point of the drug did not change during nanoformulation and extrusion.

In some embodiments, the nanoparticle form of the diclofenac has a DSC thermogram substantially as shown in FIG. 17.

In some embodiments, the nanoparticle form of the diclofenac has at least seven XRD peaks, in terms of 2-theta, selected from about 12.4°, about 16.3°, about 19.1°, about 19.4°, about 19.5°, about 19.9°, about 21.1°, about 25.5°, about 26.2°, about 27.4°, about 28.2°, and about 28.5°.

In some embodiments, the nanoparticle form of the diclofenac has at least six XRD peaks, in terms of 2-theta, selected from about 12.4°, about 16.3°, about 19.1°, about 19.4°, about 19.5°, about 19.9°, about 21.1°, about 25.5°, about 26.2°, about 27.4°, about 28.2°, and about 28.5°.

In some embodiments, the nanoparticle form of the diclofenac has at least five XRD peaks, in terms of 2-theta, selected from about 12.4°, about 16.3°, about 19.1°, about 19.4°, about 19.5°, about 19.9°, about 21.1°, about 25.5°, about 26.2°, about 27.4°, about 28.2°, and about 28.5°.

In some embodiments, the nanoparticle form of the diclofenac has at least four XRD peaks, in terms of 2-theta, selected from about 12.4°, about 16.3°, about 19.1°, about 19.4°, about 19.5°, about 19.9°, about 21.1°, about 25.5°, about 26.2°, about 27.4°, about 28.2°, and about 28.5°.

In some embodiments, the nanoparticle form of the diclofenac has at least three XRD peaks, in terms of 2-theta, selected from about 12.4°, about 16.3°, about 19.1°, about 19.4°, about 19.5°, about 19.9°, about 21.1°, about 25.5°, about 26.2°, about 27.4°, about 28.2°, and about 28.5°.

In some embodiments, the nanoparticle form of the diclofenac has at least two XRD peaks, in terms of 2-theta, selected from about 12.4°, about 16.3°, about 19.1°, about 19.4°, about 19.5°, about 19.9°, about 21.1°, about 25.5°, about 26.2°, about 27.4°, about 28.2°, and about 28.5°.

In some embodiments, the nanoparticle form of the diclofenac has at least one XRD peaks, in terms of 2-theta, selected from about 12.4°, about 16.3°, about 19.1°, about 19.4°, about 19.5°, about 19.9°, about 21.1°, about 25.5°, about 26.2°, about 27.4°, about 28.2°, and about 28.5°.

Figure 18:
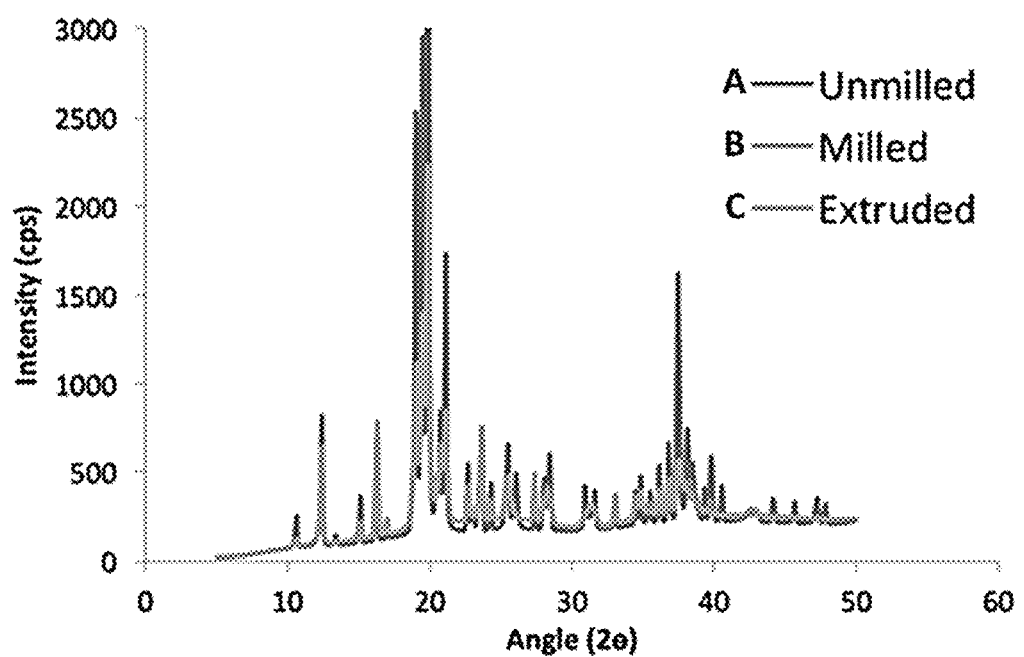
FIG. 18 shows X-ray diffraction spectra of diclofenac acid nanoformulation before milling, after milling, and after hot melt extrusion.

In some embodiments, the nanoparticle form of the diclofenac has an XRD profile substantially as shown in FIG. 18.

Figure 16:
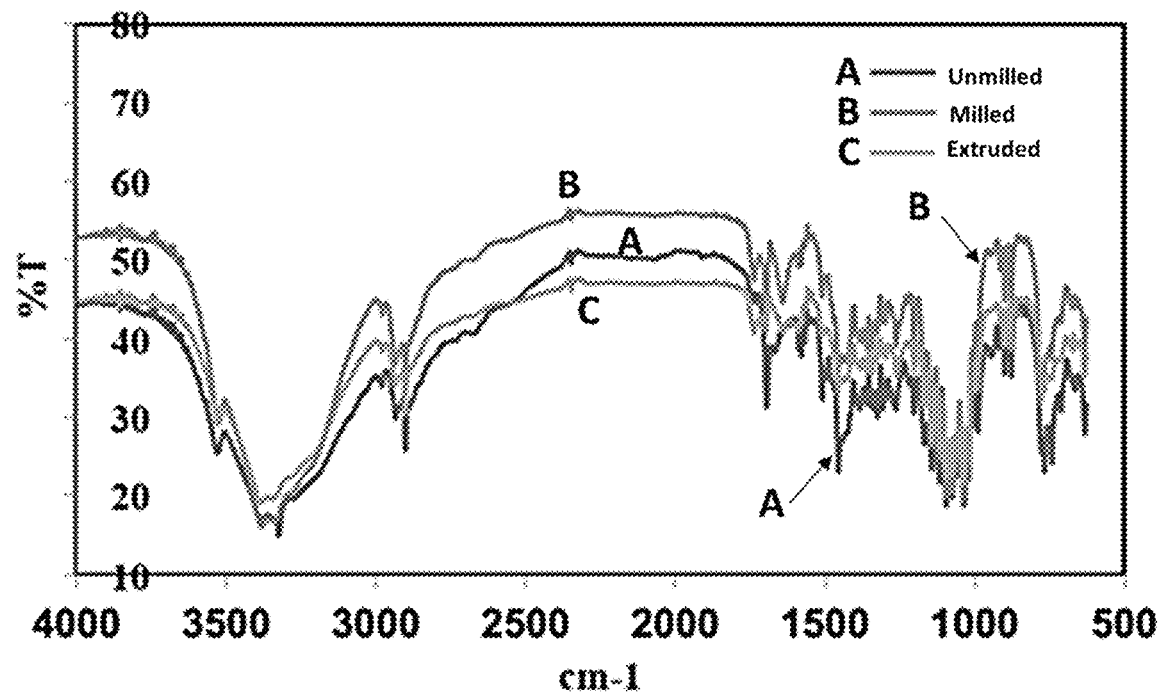
FIG. 16 shows FTIR data comparing diclofenac acid before milling, after milling, and after extrusion.

In some embodiments, the nanoparticle form of the diclofenac has an FTIR profile substantially as shown in FIG. 16.

In some embodiments, the compound is a nanoparticle form of abiraterone, or a pharmaceutically acceptable salt thereof. In some embodiments, the compound is a nanoparticle form of abiraterone acetate.

In some embodiments, the compound is a nanoparticle form of abiraterone, or a pharmaceutically acceptable salt thereof, which is crystalline. In some embodiments, the compound is a nanoparticle form of abiraterone acetate, which is crystalline.

In some embodiments, the compound is a nanoparticle form of abiraterone, or a pharmaceutically acceptable salt thereof, which is amorphous. In some embodiments, the compound is a nanoparticle form of abiraterone acetate, which is amorphous.

In some embodiments, the compound is a nanoparticle form of abiraterone, or a pharmaceutically acceptable salt thereof, which is crystalline, amorphous, or a combination thereof. In some embodiments, the compound is a nanoparticle form of abiraterone acetate, which is crystalline, amorphous, or a combination thereof.

Figure 21:
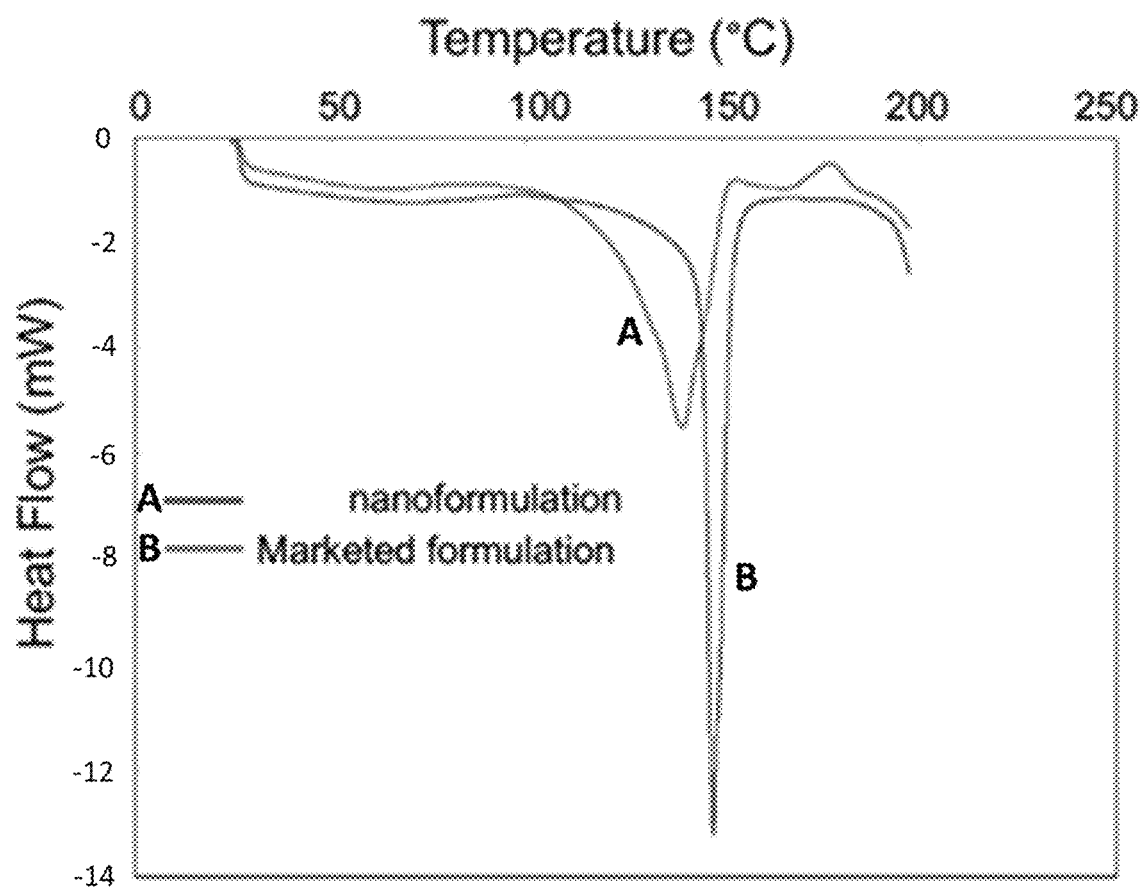
FIG. 21 shows differential scanning calorimetry data comparing the melting peaks of the abiraterone acetate nanoformulation compared to the unmilled commercially available formulation of abiraterone acetate.

In some embodiments, the nanoparticle form of the abiraterone acetate has a DSC thermogram substantially as shown in FIG. 21.

In some embodiments, the nanoparticle form of the abiraterone acetate has at least seven XRD peaks, in terms of 2-theta, selected from about.

In some embodiments, the nanoparticle form of the abiraterone acetate has at least six XRD peaks, in terms of 2-theta, selected from about 12°, about 16°, about 20°, about 21°, about 24°, and about 27°.

In some embodiments, the nanoparticle form of the abiraterone acetate has at least five XRD peaks, in terms of 2-theta, selected from about 12°, about 16°, about 20°, about 21°, about 24°, and about 27°.

In some embodiments, the nanoparticle form of the abiraterone acetate has at least four XRD peaks, in terms of 2-theta, selected from about 12°, about 16°, about 20°, about 21°, about 24°, and about 27°.

In some embodiments, the nanoparticle form of the abiraterone acetate has at least three XRD peaks, in terms of 2-theta, selected about 12°, about 16°, about 20°, about 21°, about 24°, and about 27°.

In some embodiments, the nanoparticle form of the abiraterone acetate has at least two XRD peaks, in terms of 2-theta, selected from about 12°, about 16°, about 20°, about 21°, about 24°, and about 27°.

In some embodiments, the nanoparticle form of the abiraterone acetate has at least one XRD peaks, in terms of 2-theta, selected about 12°, about 16°, about 20°, about 21°, about 24°, and about 27°.

Figure 23:
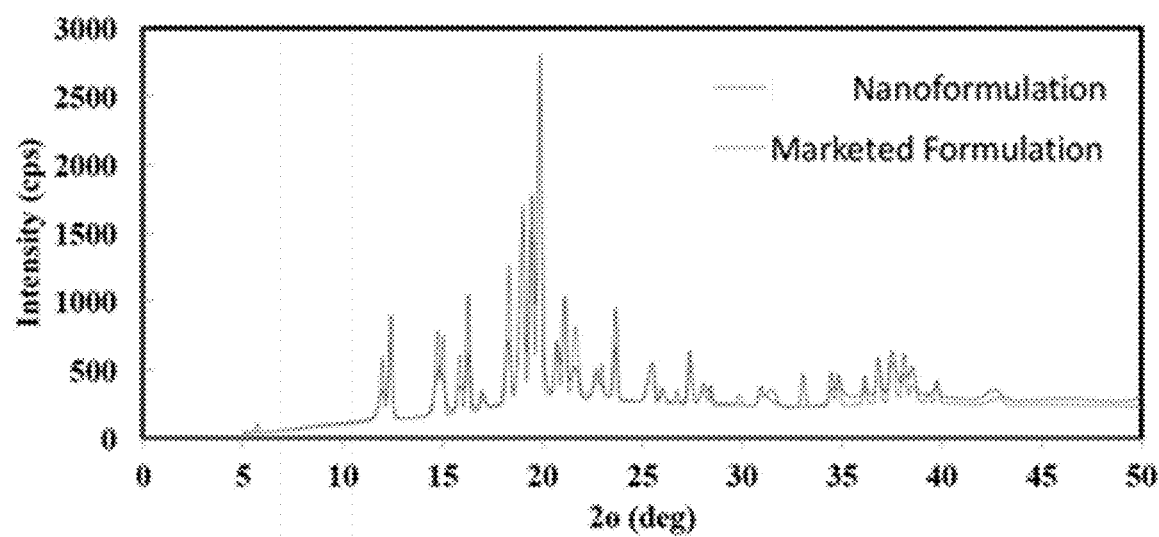
FIG. 23 shows X-ray diffraction spectra of the nanoformulation (milled) and marketed formulation (milled) of abiraterone acetate.

In some embodiments, the nanoparticle form of the abiraterone acetate has an XRD profile substantially as shown in FIG. 23.

Figure 22:
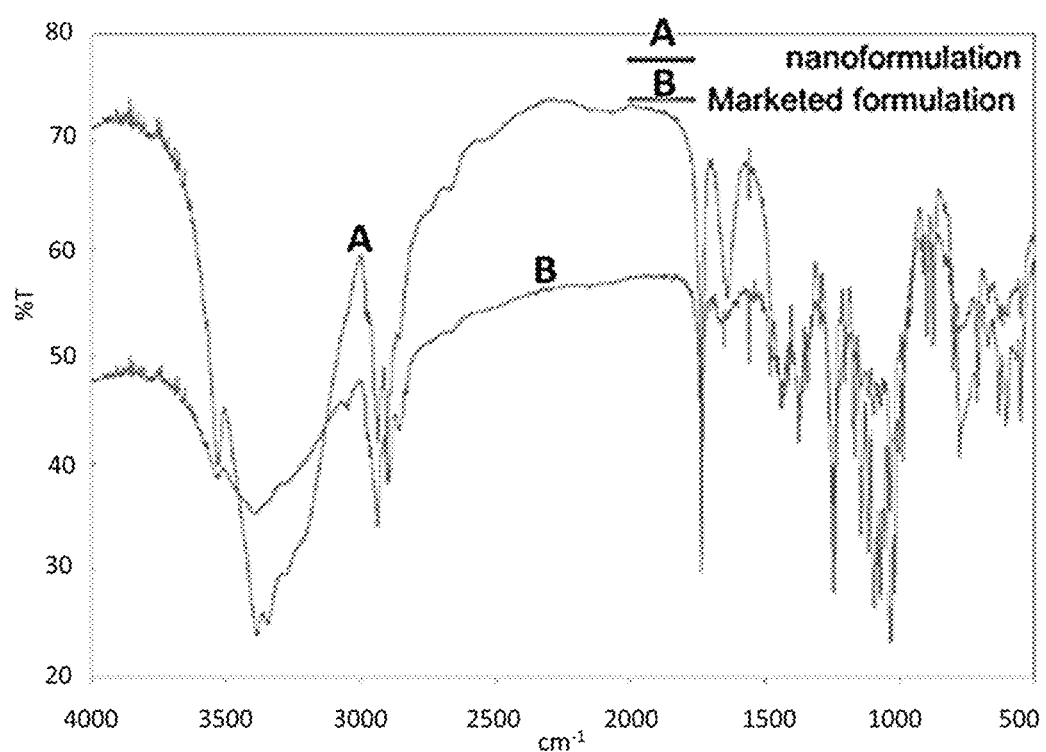
FIG. 22 shows Fourier-transform infrared (FTIR) spectroscopy data of the abiraterone acetate nanoformulation compared to the unmilled, commercially available formulation of abiraterone acetate.

In some embodiments, the nanoparticle form of the abiraterone acetate has an FTIR profile substantially as shown in FIG. 22.

The present invention also includes pharmaceutically acceptable salts of the nanoparticle compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

When employed as pharmaceuticals, the nanoparticle compounds provided herein, and salt thereof, can be administered in the form of pharmaceutical compositions; thus, the methods described herein can include administering pharmaceutical compositions provided herein. Accordingly, the present application further provides a pharmaceutical composition comprising a nanoparticle form of a compound provided herein, or a pharmaceutically acceptable salt thereof, and one or more pharmaceutically acceptable excipients. In some embodiments, the pharmaceutical composition is a nanoparticle form of the pharmaceutical composition (i.e., one or more of the components of the pharmaceutical composition is a nanoparticle component). In some embodiments, a nanoparticle form of the pharmaceutical composition is prepared according to one of more of the processes provided herein.

The nanoparticle compounds and compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Exemplary administration techniques include, but are not limited to, oral, pulmonary, rectal, colonic, parenteral, intracisternal, intravaginal, intraperitoneal, ocular, otic, local, buccal, nasal, and topical administration. In some embodiments, the nanoparticle compounds and compositions provided herein can be formulated into a dosage form selected from the group consisting of liquid dispersions, gels, aerosols, ointments, creams, lyophilized formulations, tablets, capsules; into a dosage form selected from the group consisting of controlled release formulations, fast melt formulations, delayed release formulations, extended release formulation, pulsatile release formulations, mixed immediate release, and controlled release formulations, or any combination thereof. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active nanoparticle compounds can be effective over a wide dosage range and are generally administered in a therapeutically effective amount. It will be understood, however, that the amount of the nanoparticle compound actually administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention may contain, for example, from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention may contain, for example, from about 0.1 to about 500 mg of the active ingredient. One having ordinary skill in the art will appreciate that this embodies compositions containing about 0.1 to about 100, about 0.5 to about 100, about 1 to about 100, about 10 to about 100, about 25 to about 100, about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention may contain, for example, from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the nanoparticle compounds described herein in the methods and uses of the invention.

The active compound (e.g., a nanoparticle compound provided herein) can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient (e.g., a nanoparticle compound provided herein) is mixed with a pharmaceutical excipient to form a solid formulation composition containing a homogeneous mixture of a compound of the present invention. When referring to these formulation compositions as homogeneous, the active ingredient is typically dispersed evenly throughout the composition so that the composition can be readily subdivided into equally effective unit dosage forms such as tablets, pills and capsules. This solid formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Methods of Use and Combination Therapies

The present application further provides methods of treating a disease in a subject in need thereof. As used herein, the term "subject" refers to any animal, including mammals, for example, mice, rats, other rodents, rabbits, dogs, cats, swine, cattle, sheep, horses, primates, and humans. In some embodiments, the subject is a human. In some embodiments, the method comprises administering to a subject in need thereof a therapeutically effective amount of a nanoparticle compound or pharmaceutical composition provided herein, or a pharmaceutically acceptable salt thereof. In some embodiments, the nanoparticle compound, salt thereof, or pharmaceutical composition is prepared according to one or more of the processes provided herein.

In some embodiments, the disease is selected from the group consisting of cancer, an autoimmune disease, a cardiovascular disease, a disease of the central nervous system (e.g., a neurodegenerative disease), and an inflammatory disease.

Example cancers include, but are not limited to, lung cancer, melanoma, pancreatic cancer, breast cancer, prostate cancer, liver cancer, colon cancer, endometrial cancer, bladder cancer, skin cancer, cancer of the uterus, renal cancer, gastric cancer, sarcoma, glioma, glioblastoma, or a hematological cancer (e.g., leukemia or lymphoma). In some embodiments, the disease is breast cancer.

Example diseases of the central nervous system include, but are not limited to, depression, schizophrenia, bipolar disorder, Parkinson's disease, Alzheimer's disease, and Huntington's disease.

In some embodiments, the disease of the central nervous system is selected from the group consisting of schizophrenia, bipolar disorder, Alzheimer's disease, and Huntington's disease Example inflammatory and/or autoimmune diseases include, but are not limited to, alopecia areata, autoimmune hemolytic anemia, autoimmune hepatitis, dermatomyositis, diabetes (type 1), juvenile idiopathic arthritis, glomerulonephritis, Graves' disease, Guillain-Barré syndrome, idiopathic thrombocytopenic purpura, myasthenia gravis, myocarditis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, thyroiditis, uveitis, vitiligo, and granulomatosis with polyangiitis (Wegener's granulomatosis.

Example cardiovascular diseases include, but are not limited to, coronary artery disease, high blood pressure, cardiac arrest, congestive heart failure, arrhythmia, peripheral artery disease, cardiomyopathy (e.g. dilated cardiomyopathy), ventricular fibrillation, tachycardia, myocardial infarction, long QT syndrome, Brugada syndrome, progressive cardiac conduction disease, sick sinus syndrome, atrial fibrillation, hypertension, myocarditis, and heart failure.

The phrase "pharmaceutically acceptable amount" or "therapeutically effective amount" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. For example, a "pharmaceutically acceptable amount" or "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Nanoformulation Milling Process

Milling of the solid formulation blends was performed using an attritor or ball mill. The formulation was charged into the mill, which contained steel balls in the milling chamber. Milling was performed for approximately 25-35 min and then particle size analysis of the raloxifene was performed. This sequence was repeated until the median particle size of the active pharmaceutical ingredient (e.g., raloxifene) was approximately 100 nm. In-process samples were used for measuring the particle size and size distribution throughout the size reduction process.

Example 2. Representative Nanoformulations

Three different nanoformulations were prepared with the components shown below in Table 1. The amount of sodium lauryl sulfate was kept constant in all formulations. Proportions of the raloxifene, lactose monohydrate, and copovidone were changed at two levels to maintain a specific range of particle size and distributions. The level of polymer (copovidone) was varied to ensure coating of raloxifene particles for further enhanced dissolution. Four batches were manufactured and the particle size distribution of all four batches was measured. All four batches had similar particle size and distributions, which demonstrated process robustness. Of the four batches, the formulation with the highest drug load and lowest lactose monohydrate content was used for further analytical testing as described below in Examples 3-8. The components of the nanoformulation used for further testing are shown below in Table 1.

TABLE 1

Nanoformulation Components

| Component | % Composition |
|---|---|
| Raloxifene Hydrochloride | 15% |
| Copovidone (KollidonVA64) | 6% |

TABLE 1-continued

Nanoformulation Components

| Component | % Composition |
|---|---|
| Sodium Lauryl Sulfate | 1% |
| Lactose Monohydrate | 78% |

Example 3. Particle Size Analysis

Particle size of the nanoformulations was determined by laser diffractometer (Model: S3000). The particle size and distribution was obtained based on number distribution and the values were the average of three measurements. A standard particle size sample preparation recipe was used to perform particle size analysis.

FIG. 1 shows the particle size of a marketed raloxifene formulation (i.e., an un-milled formulation) and particle size and distributions of representative raloxifenenano formulations (i.e., milled formulations) of the present invention. FIG. 1 also shows the particle size d50 of drug before and after milling where the proportions of raloxifene and excipients were the same for both formulations. The particle size d50 of the nanoformulation was about 280 times smaller than the d50 of unmilled formulation. The d50 of unmilled formulation was about 35 microns.

Example 4. Melting Point and Crystallization

Thermal curves of the milled nanoformulation and unmilled formulation were recorded by a differential scanning calorimeter. Each sample (~5 mg) was scanned in an aluminum pan at a heating rate of 5° C./minute over the range of 25-400° C. with an empty aluminium pan used as reference. Samples were heated under nitrogen atmosphere.

Differential scanning calorimetry (DSC) studies were performed on the milled nanoformulation and un-milled formulation in the solid state, as shown in FIG. 2. Endothermic peaks for excipients and raloxifene showed a single peak for both formulations. The sharp peaks for excipients and raloxifene confirmed that raloxifene and excipients were in a crystal state before and after milling. The melting peaks of raloxifene before and after milling were almost at the same temperature, which confirms that crystal form of raloxifene did not change throughout the nanoformulation process.

Example 5. Fourier Transform Infrared Spectroscopy

The identity of raloxifene was determined on un-milled and milled nanoformulations to verify that the structure of the therapeutic agent did not change during milling. The Fourier transform infrared spectroscopy (FTIR) spectra of the milled nanoformulation and un-milled formulation were obtained by conventional KBr pellet method. The scanning range was 4000-550 cm$^{-1}$. A total of 16 scans were performed.

FTIR studies showed that there was no significant change in the spectrum of raloxifene in the un-milled formulation and the milled nanoformulation. The absence of shifts in wave numbers of the FTIR peaks, as shown in FIG. 3, from the un-milled formulation and milled nanoformulation shows the lack of significant interaction between the drug and other formulation components; thus, these results showed the absence of form change of raloxifene before and after milling or any well-defined interaction between raloxifene and other components of the formulation.

Example 6. In-Vitro Dissolution

In-vitro dissolution testing was performed by following the United States Pharmacopeia (USP) Apparatus II at 50 rpm with 1000 mL of water with 0.1% Tween 80 at body temperature. Three samples of each nanoformulation and un-milled formulation containing powder samples equivalent to 60 mg raloxifene were tested. The samples of dissolution media were removed using an automated sampling system at a predetermined time interval (10, 20, 30, 45 min). The collected samples were analyzed using a UV-spectrophotometer after sufficient dilution at $\lambda_{max}$=290 nm.

Figure 4:
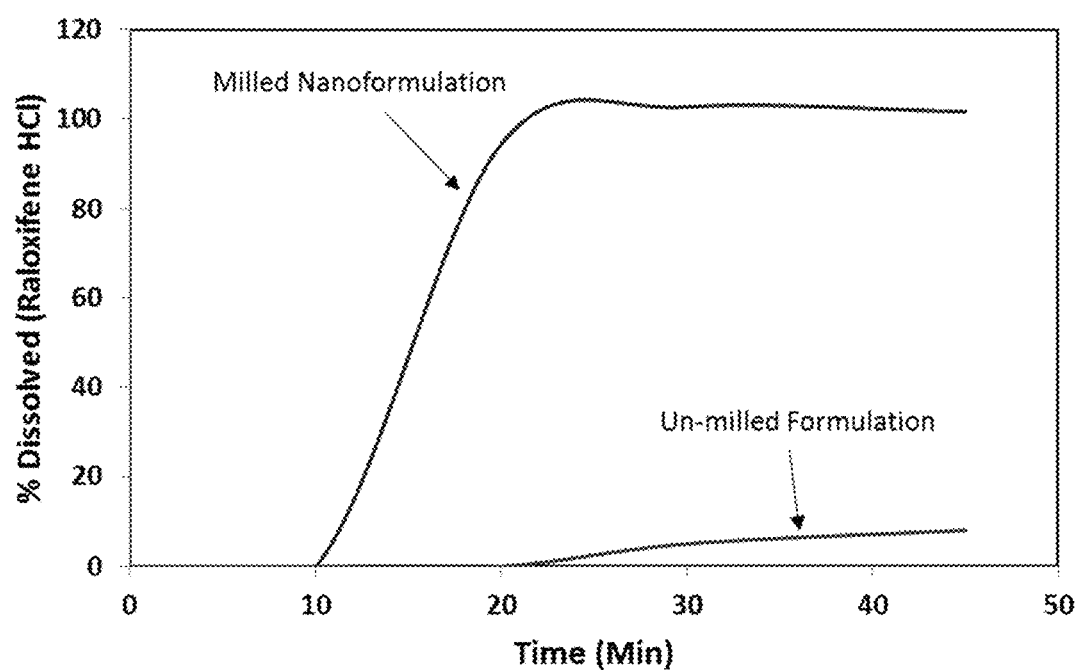
FIG. 4 shows a comparison of dissolution profiles of a nanoformulation of raloxifene HCl prepared according to a milling process provided herein and an un-milled formulation.

The results of dissolution studies of the milled nanoformulation and un-milled formulation are shown in Table 2 and FIG. 4. The dissolution of the milled nanoformulation after 45 minutes was about 12 times higher than the dissolution of the un-milled formation. The results of dissolution studies showed that the dissolution of the milled nanoformulation was substantially higher than the un-milled formulation. The results show that the solubility of the nanoformulation was substantially enhanced by the milling process compared to an un-milled formulation.

TABLE 2

Results of Dissolution Studies of Milled Nanoformulations and Un-milled Formulations

| Sample Description | Time (min) | Average (% dissolved) |
|---|---|---|
| Milled Nanoformulation | 10 | 94.3 ± 5% |
| | 20 | 102.6 ± 7% |
| | 30 | 101.6 ± 3% |
| | 45 | 100.5 ± 5% |
| Un-milled Formulation | 10 | 0 ± 2% |
| | 20 | 0 ± 3% |
| | 30 | 5 ± 4% |
| | 45 | 8 ± 5% |

Example 7. X-Ray Diffraction

Powder crystal (XRD) patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. The diffraction patterns were collected using a scanning position-sensitive detector (X'Celerator) located 240 mm from the specimen and Data Collector software.

The XRD studies were undertaken to consolidate the DSC data indicating the crystallinity of un-milled raloxifene formulations and milled nanoformulations. The diffraction spectrum of un-milled and milled raloxifene formulations showed that crystallinity was unchanged, as shown by numerous distinct peaks in FIG. 5. No new peaks were observed upon analysis of the milled nanoformulation, showing the absence of interactions between the drug and the other components of the nanoformulation during the milling process. The prominent peaks from raloxifene in the milled nanoformulation and un-milled formulation were present at similar positions in the XRD spectra which further supported the data shown in the DSC measurements.

Example 8. In-Vivo Assays

Figure 6:
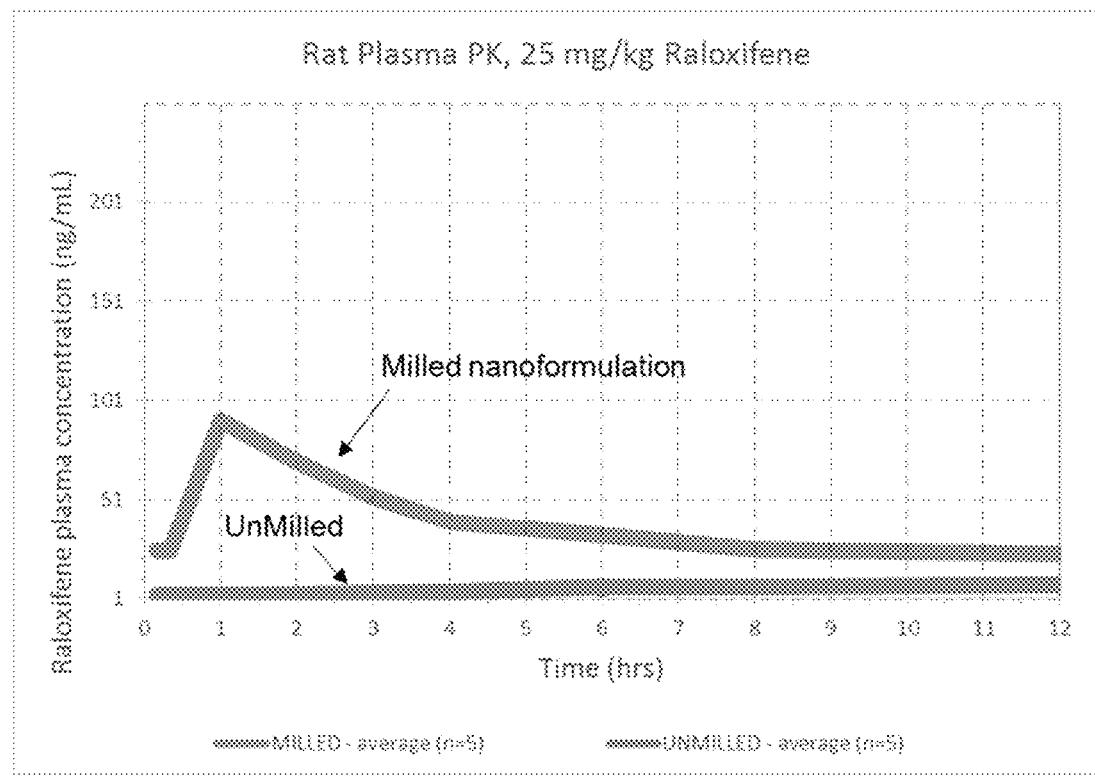
FIG. 6 shows a comparison of raloxifene plasma concentration for rats administered the milled nanoformulation of raxolifine provided herein (25 mg/kg) or an unmilled formulation of raloxifene.

FIG. 6 shows a comparison of raloxifene plasma concentration for rats administered the milled nanoformulation of raxolifine (22 mg/kg) or an unmilled formulation of raloxifene. Table 3 shows a list of representative PK parameters measured for the milled nanoformulation of raxolifine and an unmilled formulation of raloxifene.

TABLE 3

| PK Parameters | NON-MILLED | | MILLED | |
|---|---|---|---|---|
| | Mean (n = 5) | Standard Deviation | Mean (n = 5) | Standard Deviation |
| $T_{max}$ (h) | 7 | 1 | 3 | 2 |
| $C_{max}$ (μg/mL) | 8 | 4 | 127 | 120 |
| $C_{last}$ (concentration at $T_{last}$; ng · mL$^{-1}$) | 7 | 3 | 24 | 12 |
| $AUC_{last}$ (area under the curve; 0-$T_{last}$; ng · mL$^{-1}$ h] | 41 | 18 | 338 | 141 |

Example 9. Scale-Up Analysis

Diclofenac acid was used as a model compound for establishing commercial scale parameters of the nanoformulation milling process described in Example 1. Diclofenac acid was selected based on several considerations, such as poor solubility in water. Forty formulations (pre-milling) of diclofenac acid were prepared and analyzed. The composition of each formulation varied according to drug load, polymer selection, and load, and surfactant selection and load. The percent composition of fillers was adjusted for individual formulations. Additionally, each individual formulation was subjected two distinct milling conditions, which resulted in 48 distinct diclofenac nanoformulations. These formulations were nanoformulated according to the general milling conditions described below, using an outside (jacket) temperature of 11° C.-17° C. and temperature was controlled using external chiller. The variables for preparing the nanoformulations are further summarized below:

Formulation Composition
Active Drug
  Diclofenac acid drug load: 10%, 12%, or 15%
Excipient Selection
  Polymers (10% and 12% of formulation w/w)—Kollidon VA64 or Soluplus
  Surfactant (0.5% and 1%)—Sodium lauryl sulfate or poloxamer 188
  Filler—lactose monohydrate or mannitol
Milling Conditions
  Large mill—500 g batch at 250 rpm and 300 rpm; 1000 g batch at 300 rpm
  Milling media: Stainless steel balls of two distinct diameters were used at a 1:3 ratio (large diameter:small diameter). 20 lbs of milling media was used for 500 g batch and 40 lbs milling media was used for 1 kg batch. Due to the shear and impact mechanisms of milling, milling media at this ratio produced nanoformulations in the d50 size range of 100 nm-200 nm.
  Milling time intervals: 10 min, 15 min, 20 min, 25 min, 30 min, and 35 minutes. Most formulations were milled up to 35 minutes and particle size data collected for two time points: 30 minutes and 35 minutes.

Collectively, the experimental framework and variables outline above resulted in the preparation of 40 individual formulations for two distinct milling conditions, resulting in a total of 64 milled nanoformulations. In total, 128 product samples were evaluated for product size using a mastersizer laser diffractometer to examine the particle size and size range that was achieved using the various formulations.

Figure 7:
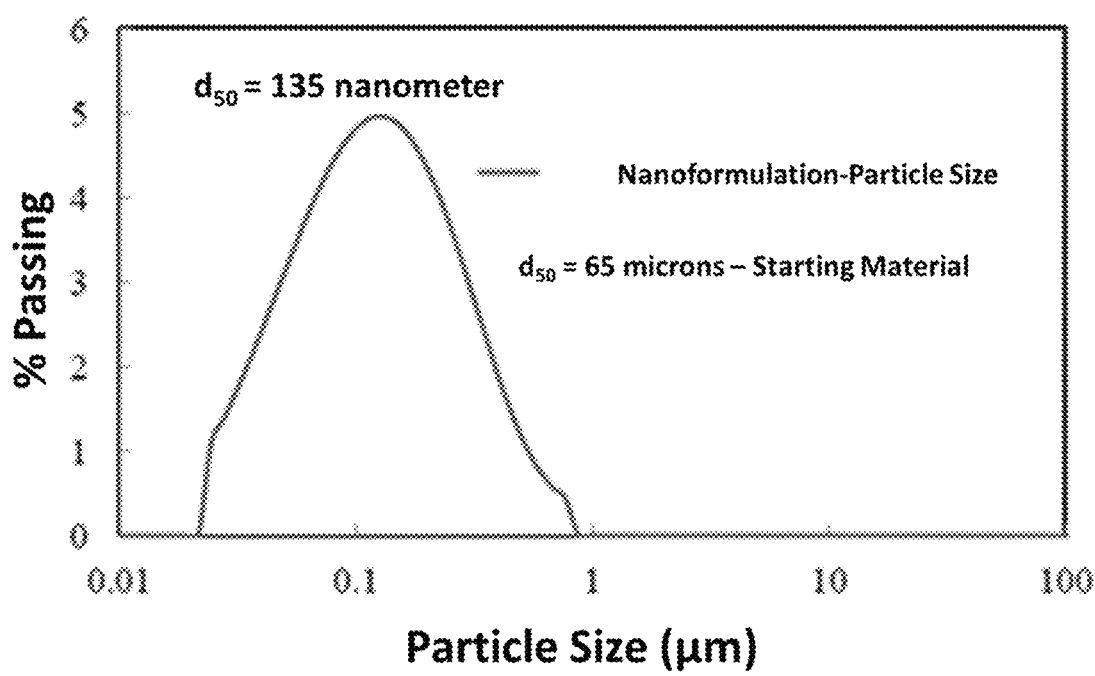
FIGS. 7-8 show representative examples of the particle size/size-distributions of the diclofenac acid nanoformulation. Data were acquired using a Mastersizer M3000 laser diffractometer.
Figure 8:
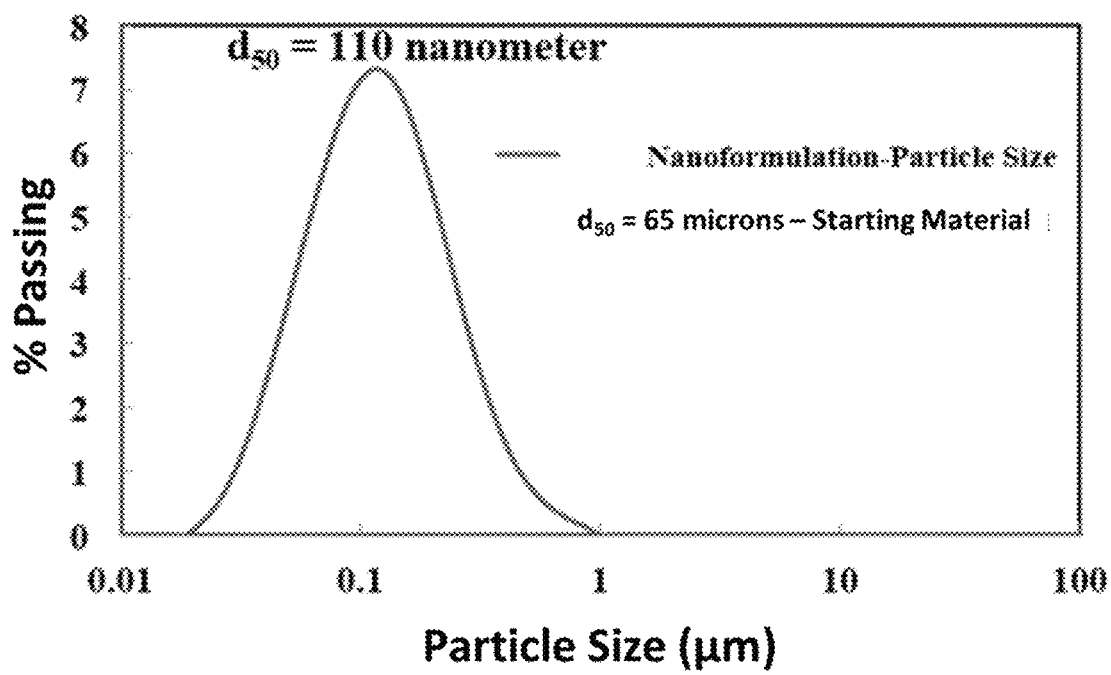

As shown in FIG. 7 the target d50 range was achieved after 35 minutes of milling diclofenac acid crystals, using a 15% drug load (highest), and 10% polymer in the formulation. In FIG. 8, the target d50 range was achieved after 35 minutes of milling diclofenac acid crystals, using a 10% drug load (lowest), and 10% polymer in the formulation. Minor variability was observed in the final d50 and size-distribution after independent iterations of formulation blending and milling (FIGS. 7-8). However, a d50 in the target range was consistently achieved using the diclofenac acid formulation and processing parameters described above.

Figure 9:
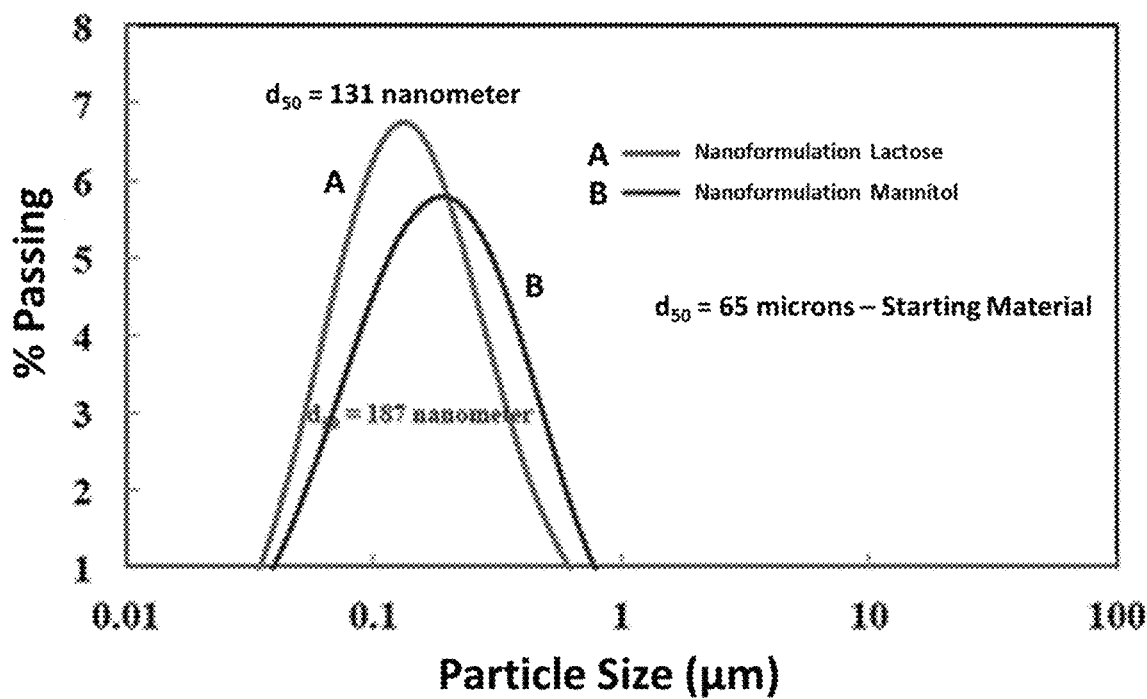
FIG. 9 shows particle size/size-distributions of the diclofenac acid nanoformulation using lactose monohydrate and mannitol as fillers. Data were acquired using a Mastersizer M3000 laser diffractometer.

The representative data in FIGS. 7-8 were derived from formulations containing lactose monohydrate as the filler. However, the effect of fillers in the final particle size and size distribution was also investigated. It was observed that use of mannitol in the formulation yielded, on average, larger particle size than formulations containing lactose monohydrate (FIG. 9). This effect of mannitol often prevented achieving a target particle size d50 in the range of 100-200 nm; whereas, formulations containing lactose monohydrate as the filler yielded the target d50 across a relatively robust set of operating conditions.

Figure 10:
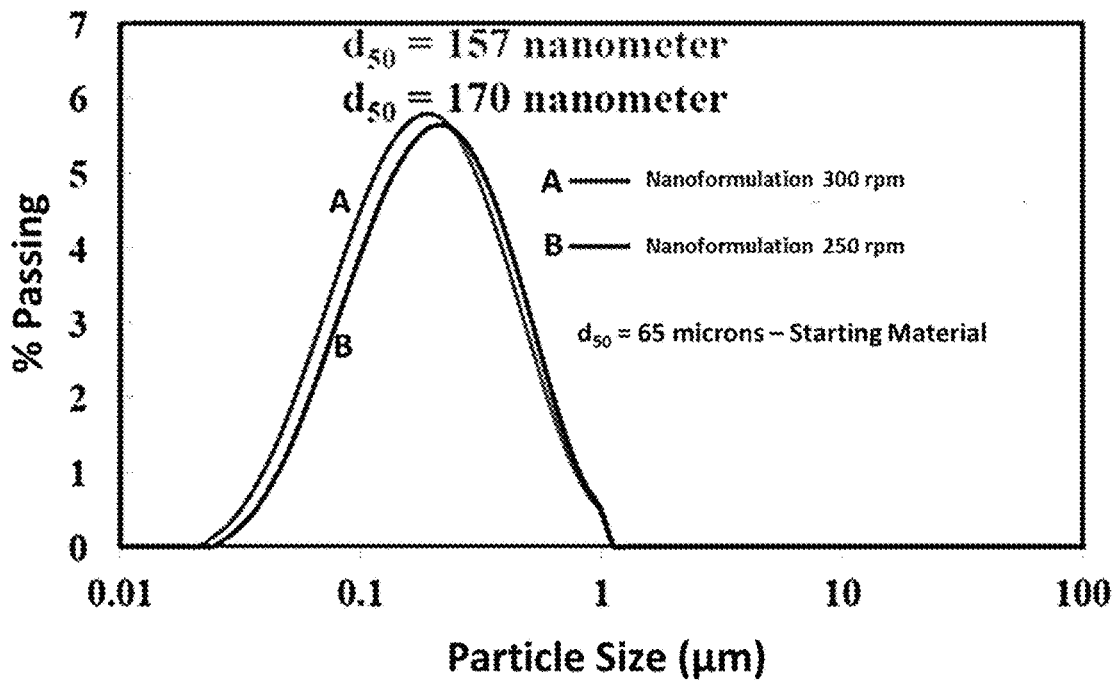
FIG. 10 shows particle size/size-distributions of the diclofenac acid nanoformulation using distinct milling speeds. Data were acquired using a Mastersizer M3000 laser diffractometer.
Figure 11:
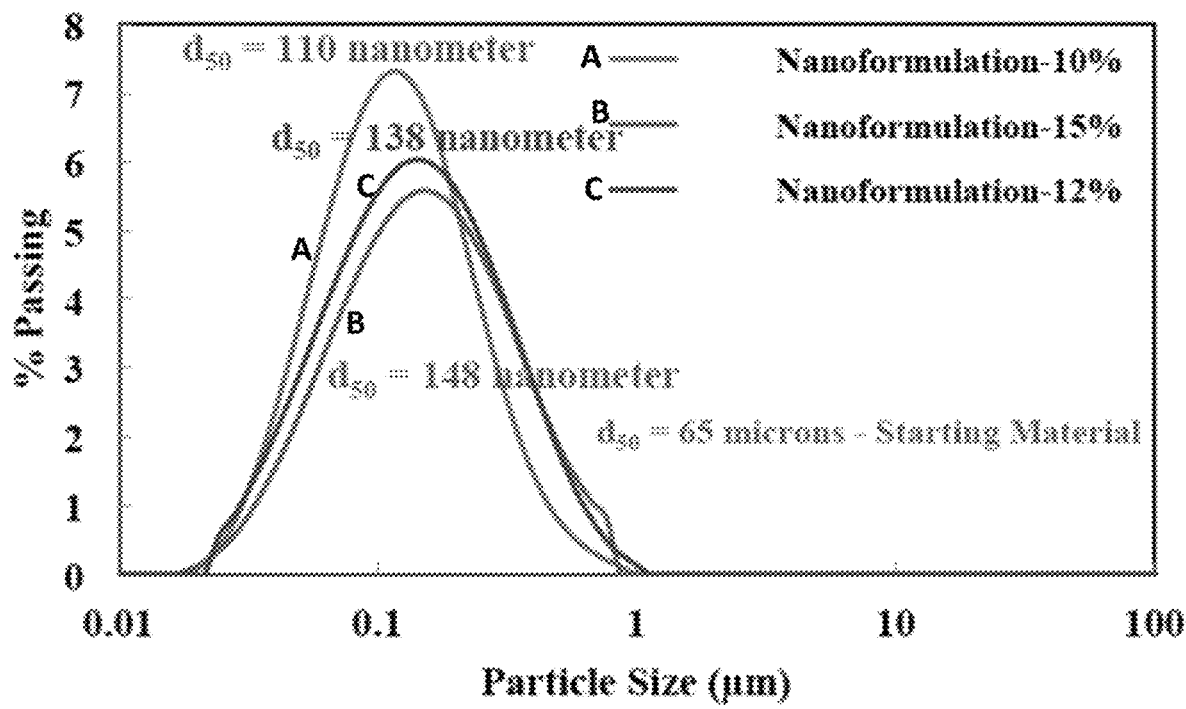
FIG. 11 shows particle size/size-distributions of the diclofenac acid nanoformulation under various drug loading conditions. Data were acquired using a Mastersizer M3000 laser diffractometer.

Next, a series of studies was conducted to determine the effect of other parameters, including mill speed and drug loading (FIGS. 10-11). Collectively, these studies established the proof of concept for achieving the target d50 under a defined range of operating conditions, using the model compound diclofenac acid. The typical particle sizes of diclofenac acid given below is similar to the particle size of raloxifene hydrochloride, abiraterone acetate, and sunitinib malate using the same parameters.

In summary, the data from diclofenac acid demonstrated that the following parameters have little to no effect on d50 of the drug particle size after milling:
  Starting particle size of drug (e.g., the starting particle sizes of diclofenac acid, abiraterone acetate, raloxifene hydrochloride, and sunitinib malate tested were different)
  Surfactant concentration (0.5% and 1.0% w/w)
  Polymer loading (10% and 12% w/w)

In contrast, the data from diclofenac acid experiments demonstrated that the following parameters exhibited a significant measurable effect on d50 of the drug particle size after milling:
  Drug loading
  Polymer type
  Type of filler
  Milling time As discussed above, two distinct polymers were used (Kollidon VA64 or Soluplus) at two loadings of 10% and 12% (w/w basis) in preparing the investigational formulations. Excipients, and the polymers in particular, were selected based on the melting point differential relative to the active pharmaceutical ingredient (API) diclofenac acid, which has a melting point of 170° C.

Melt Extrusion Analysis

After developing candidate formulations to achieve desired particle sizes and size ranges, parameters for hot melt extrusion of a larger-scale 500 g batch size were investigated. A small set of temperature range optimization studies were first performed to select a temperature range of extrusion of the nanomilled formulations. Based on these pilot studies, two different conditions were used for hot melt extrusion:

20 rpm and 40 rpm, with target feed rate of 0.5 kg and 1 kg per hour.

Extrusion zone temperatures were specific to polymers in the formulation. Formulations containing Kollidon VA64 (melting point 145° C.) were extruded at 135° C.-145° C. After 10 minutes of operation, the temperature was lowered to compensate for heat generated during mixing of twin screws in the hot melt extruder barrel. Formulations containing Soluplus (melting point 120° C.) were extruded at 110-120° C.

The actual feed rate achieved using these conditions was 0.18 kg/hour and 0.24 kg/hour using the above-indicated rpm parameters, respectively. These studies generated a total of 256 experiments and polymer-coated formulations. These 256 samples were generated from a total of 64 feed samples, which were derived from the 40 distinct nanoformulations. Representative dissolution data of the resulting polymer-coated nanoformulations are shown in FIGS. 12-15.

Figure 12:
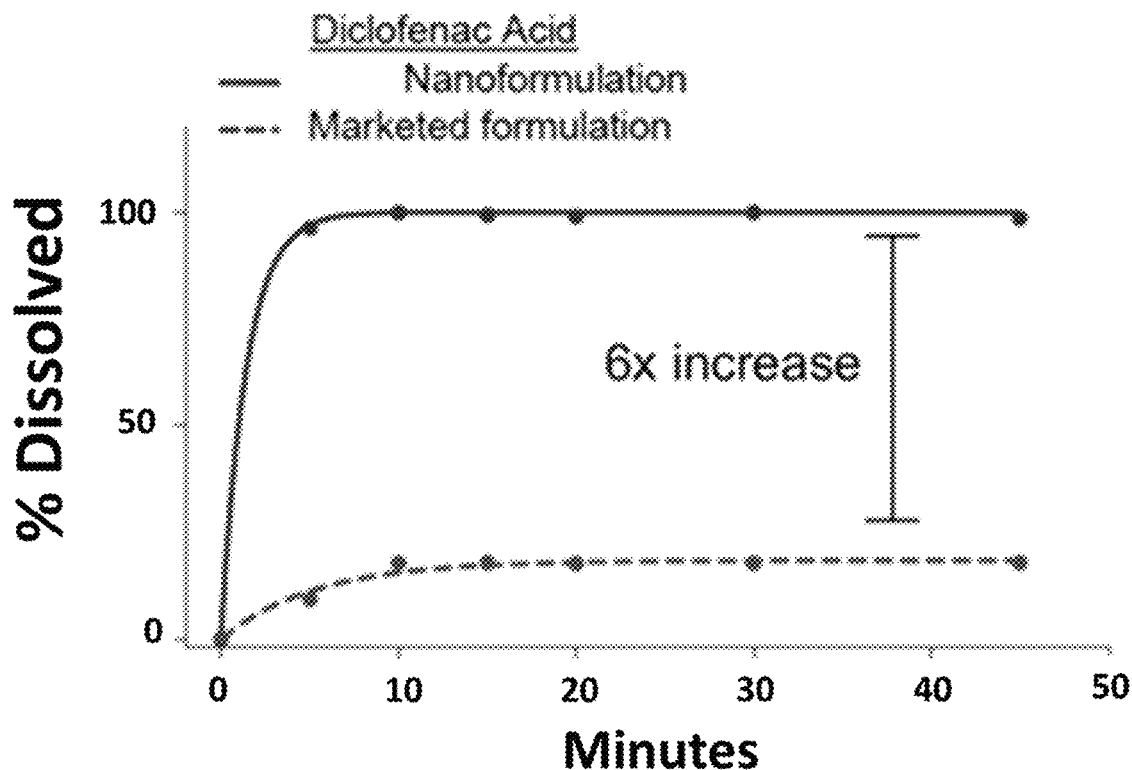
FIG. 12 shows dissolution of the diclofenac acid nanoformulation (15% drug loading) relative to the commercially available formulation. Data are for 15% drug loading formulation, unless otherwise specified.
Figure 13:
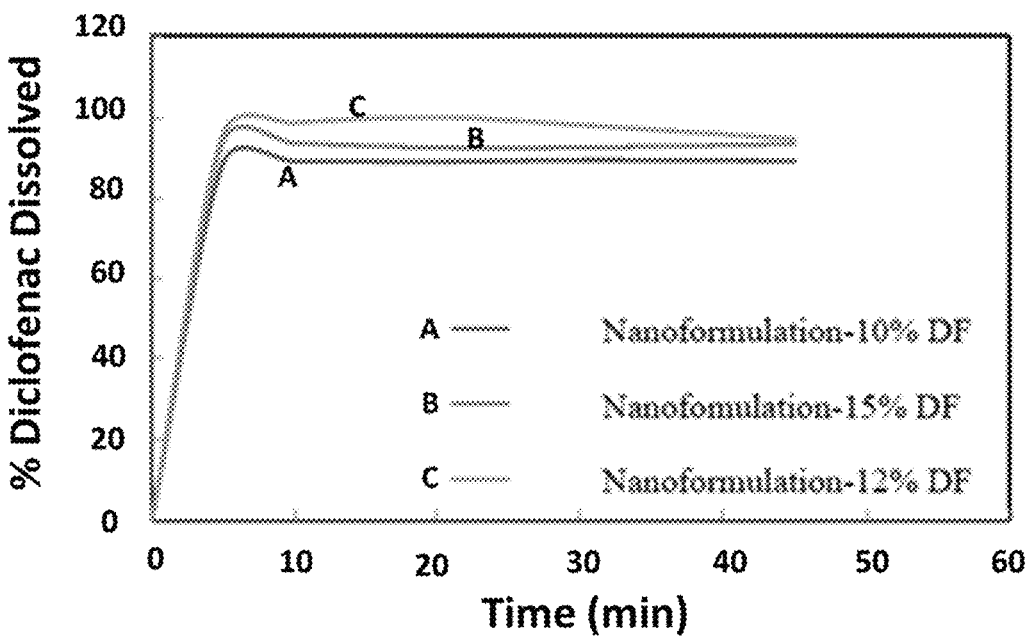
FIG. 13 shows dissolution of the diclofenac acid nanoformulation relative to the commercially available formulation under various drug loading conditions.
Figure 14:
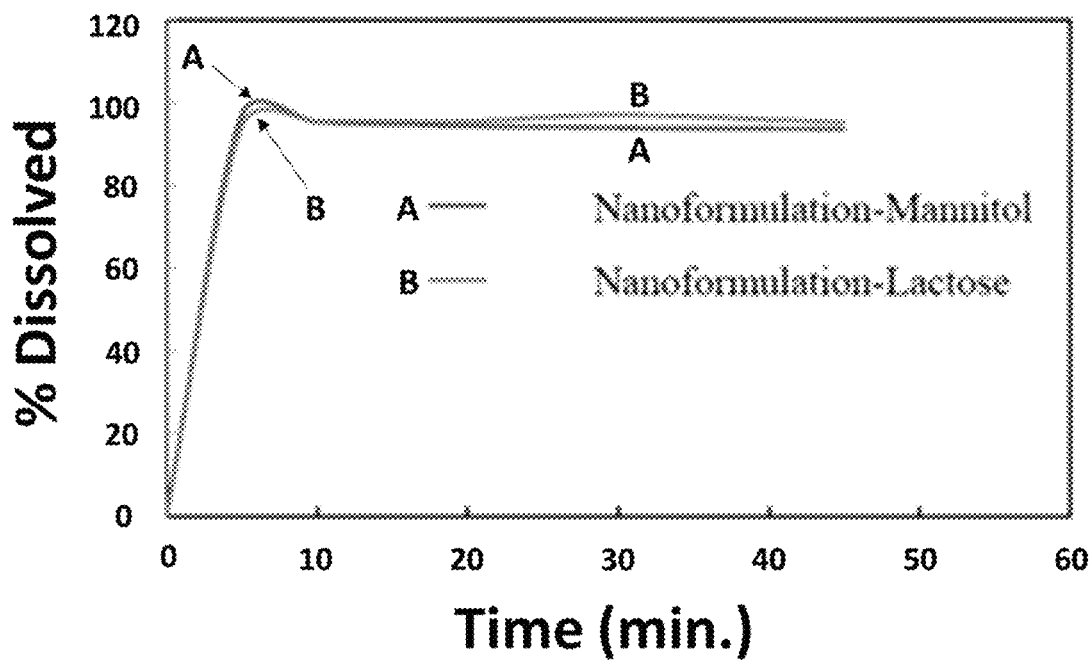
FIG. 14 shows dissolution of the diclofenac acid nanoformulation relative to the commercially available formulation using either lactose monohydrate or mannitol as the filler.
Figure 15:
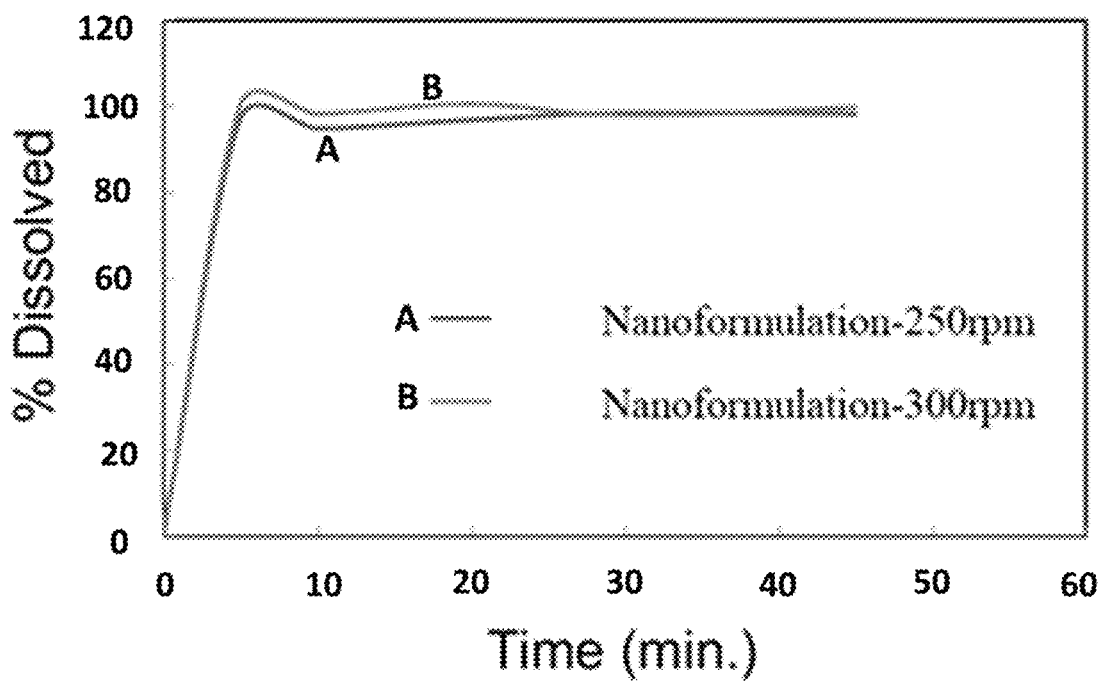
FIG. 15 shows dissolution of the diclofenac acid nanoformulation relative to the commercially available formulation when milling is performed at either 250 rpm or 300 rpm.

Relative to the corresponding commercially available formulation, the nanoformulated diclofenac acid described herein (15% drug loading and 10% polymer) showed markedly improved dissolution (FIG. 12). Similar improvements in dissolution were observed with diclofenac acid nanoformulation of 10%, 12%, or 15% drug loading (FIG. 13). Pilot studies were also performed using 12% polymer (16 different formulations) in the final formulation. It was observed that 10% polymer was sufficient to confer drastically increased dissolution relative to the commercially available formulation. The use of specific fillers (lactose monohydrate or mannitol) or differences in mill speed similarly increased the dissolution of diclofenac relative to the unmilled formulation, and were not associated with differences in dissolution improvements between conditions (FIGS. 14-15).

Various techniques were used to characterize the crystal identity of the extruded nanoformulations and to confirm uniform polymer coating on the nano-sized crystals, including Fourier Transform-Infrared Spectroscopy (FTIR), differential scanning calorimetry (DSC), and X-ray diffraction (XRD) to investigate possible form changes of the crystal that may have occurred during the milling and extruding processes.

FTIR data revealed no differences in the spectrum or numbers of distinct peaks, suggesting an absence of interaction between the drug and excipients (FIG. 16). Furthermore, DSC data demonstrated that the unmilled, milled, and extruded material exhibited distinct and similar melting point peaks, suggesting that the crystal form was unchanged (FIG. 17). Similarly, XRD spectra demonstrated consistent peaks in the unmilled, milled, and extruded material, as shown below in Table 4.

TABLE 4

| 2θ (deg) | Unmilled Intensity (cps) | Milled Intensity (cps) | Extruded Intensity (cps) |
|---|---|---|---|
| 12.4 | 816.9 | 555.9 | 639.5 |
| 16.3 | 688.0 | 678.7 | 760.0 |
| 19.1 | 2482.8 | 964.0 | 1114.1 |
| 19.4 | 2361.3 | 1171.6 | 1134.0 |
| 19.5 | 2948.8 | 1243.8 | 1365.4 |
| 19.9 | 7919.2 | 1824.3 | 2234.4 |
| 21.1 | 1732.0 | 622.5 | 844.3 |
| 25.5 | 658.5 | 419.2 | 481.5 |
| 26.2 | 339.3 | 251.1 | 248.0 |
| 27.4 | 409.1 | 407.6 | 478.5 |
| 28.2 | 328.2 | 404.9 | 377.8 |
| 28.5 | 589.4 | 381.5 | 343.8 |

Figure 19:
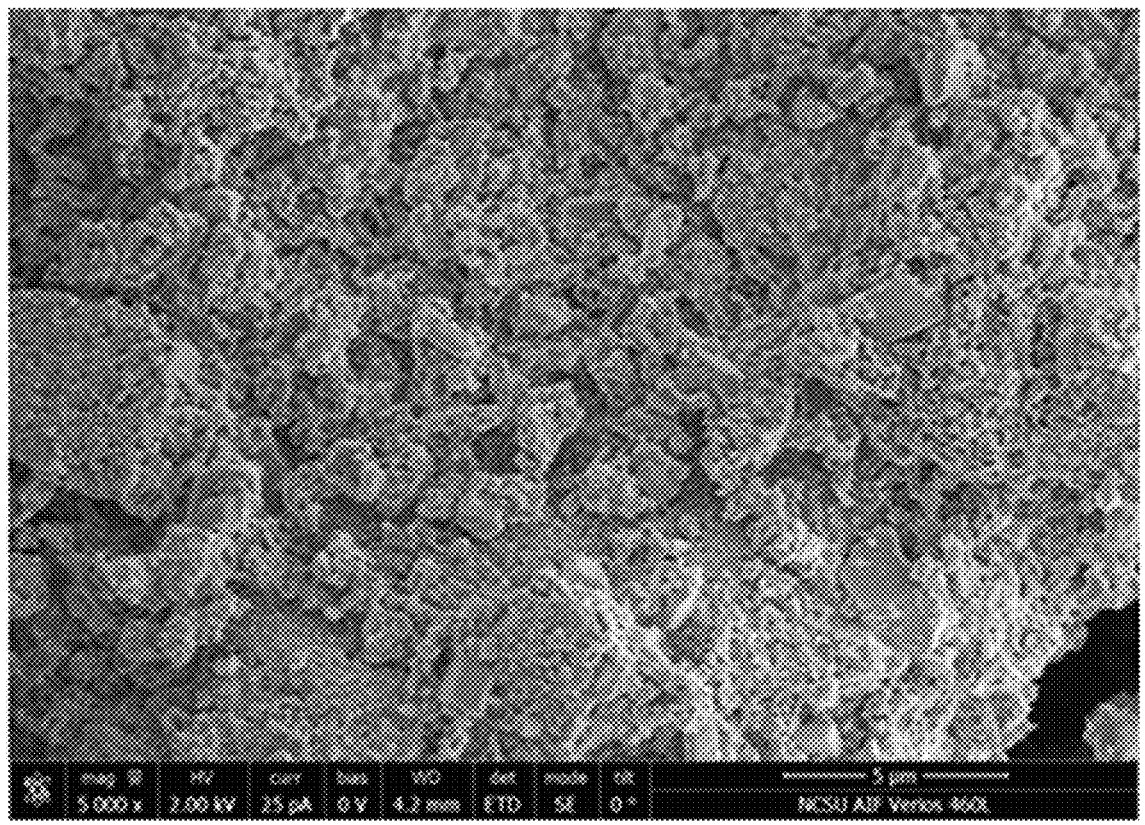
FIG. 19 shows a scanning electron microscopy micrograph of polymer-coated diclofenac acid nanocrystals after hot melt extrusion.

The prominent peaks of diclofenac acid from the milled and unmilled formulation were clearly seen at similar positions, demonstrating that the crystallinity was unchanged during the nanoformulation process (FIG. 18). Finally, used scanning electron microscopy (SEM) was used to confirm uniform polymer-coating of the nanocrystals after extrusion. SEM micrographs revealed that nanocrystals were coated with polymer in the extruded product and that drug particles adsorbed to the surface of polymer which kept the particles in discrete state and prevented them from agglomeration and aggregation (FIG. 19).

Additionally, it was found that several formulations containing mannitol as the filler demonstrated caking problems during the milling process, which decreased product yield (~300 g nanomilled material from a 500 g batch) for subsequent feeding into extruder. This issue did not occur with formulations containing lactose monohydrate as the filler. Further, it was found that humidity control was not necessary to achieve target product profiles.

Example 10. Nanoformulation of Abiraterone Acetate

Figure 20:
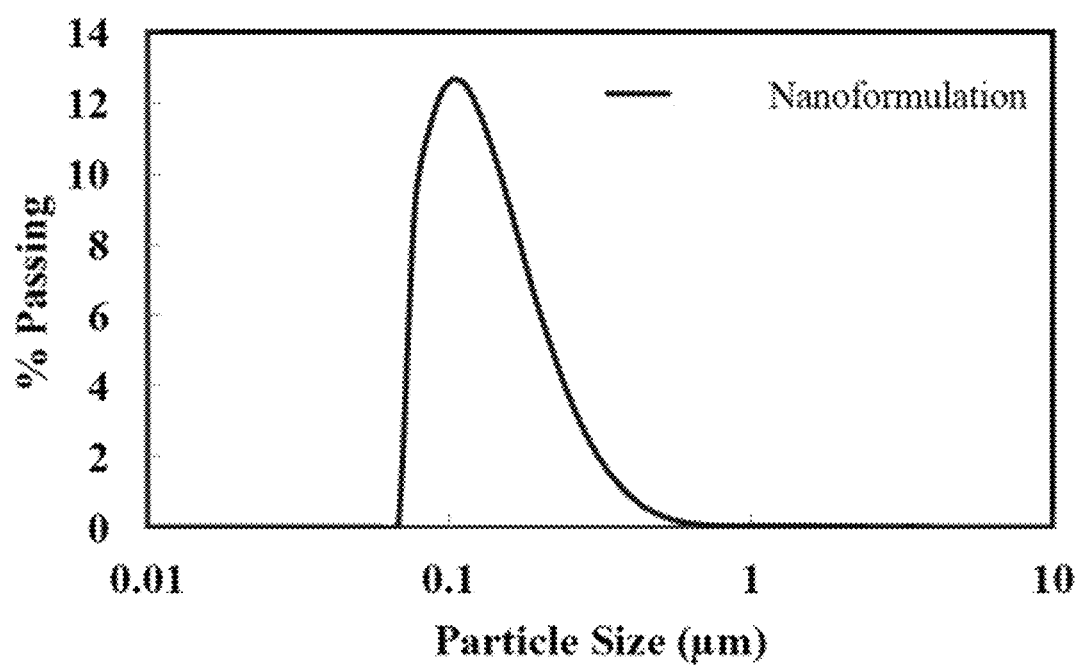
FIG. 20 shows particle size and distributions of an abiraterone acetate nanoformulation. Data were acquired using a Mastersizer M3000 laser diffractometer.

Based on our results described in Example 9, the experimentally determined formulation parameters were used to generate a nanoformulation of the prostate cancer drug abiraterone acetate. Similar to diclofenac and raloxifene HCl, nanomilling of an abiraterone acetate formulation yielded a milled product within the target $d_{50}$ and a narrow size distribution, as shown in FIG. 20. Differential scanning calorimetry (DSC) studies were performed on the nanoformulation and un-milled formulation in the solid state, as shown in FIG. 21, and endothermic peaks for excipients and abiraterone acetate showed a single peak for both formulations. The sharp peaks for excipients and abiraterone acetate confirmed that abiraterone acetate and excipients were in a crystal state before and after milling, and the melting peaks at similar temperatures confirmed that crystal form of abiraterone acetate did not change during the nanoformulation process.

FTIR studies showed that there was no significant change in the spectrum of abiraterone acetate in the commercially available formulation (i.e., before milling) and nanoformulation (i.e., after milling). The absence of shifts in wave numbers of the FTIR peaks from the commercially available formulation and nanoformulation indicated the lack of significant interaction between the drug and excipients, as shown in FIG. 22. These results demonstrate the absence of form change of abiraterone acetate before and after milling or any well-defined interaction between abiraterone acetate and excipients used in the formulation.

Next, X-ray diffraction studies were conducted on the nanoformulation of abiraterone acetate and the commercially available formulation. These studies were undertaken to cross-verify the DSC data, which indicated that the crystallinity of abiraterone acetate before and after milling and coating was unchanged. Similarly, the diffraction spectrum of unmilled and milled abiraterone acetate showed that crystallinity was unchanged, as demonstrated by numerous distinct peaks observed in FIG. 23. No new peaks could be observed, suggesting the absence of interaction between the drug and the carrier. The prominent peaks from abiraterone acetate from the milled and unmilled formulation were clearly seen at similar position, demonstrating that the crystallinity was unchanged during the nanoformulation process. Representative 2-theta peaks observed in the XRD analysis are shown below in Table 5.

TABLE 5

| 2-theta (°) | Intensity (cps; NanoFormulation) | Intensity (cps; Commercial Formulation) |
| --- | --- | --- |
| 12 | 902 | 706 |
| 16 | 1053 | 788 |
| 20 | 2754 | 1244 |
| 21 | 1035 | 981 |
| 24 | 952 | 672 |
| 27 | 6307 | 560 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A continuous process, comprising:
   i) milling a pharmaceutical composition in a ball milling apparatus to produce a milled nanoparticle form of the pharmaceutical composition; wherein the milling is performed in the absence of a solvent component; and
   ii) coating the milled nanoparticle form of the pharmaceutical composition with one or more polymers to yield a coated nanoparticle pharmaceutical composition comprising about 10% w/w to about 12% w/w polymer, wherein the coating is performed using a melt extrusion process, a melt blown process, a spunbond process, or a high temperature milling process;
   wherein the pharmaceutical composition comprises a therapeutic agent selected from dasatinib, abiraterone, raloxifene, capecitabine, methotrexate, diclofenac, and prednisone, or a pharmaceutically acceptable salt thereof, and one or more pharmaceutically acceptable excipients.

2. The process of claim 1, wherein the pharmaceutical composition comprises a solid mixture of the therapeutic agent and one or more pharmaceutically acceptable excipients.

3. The process of claim 1, wherein prior to the milling of step i), the median particle size of the pharmaceutical composition or therapeutic agent is from about 1 to about 1000 μm.

4. The process of claim 1, wherein the milled nanoparticle form of the pharmaceutical composition comprises a surface area which is about 2 to about 400 times greater than the surface area of the pharmaceutical composition or therapeutic agent prior to milling.

5. The process of claim 1, wherein the bioavailability of the therapeutic agent, or a pharmaceutically acceptable salt thereof, is increased by about 2 fold to about 20 fold compared to the therapeutic agent prior to performing the process.

6. The process of claim 1, wherein the solubility of the therapeutic agent, or a pharmaceutically acceptable salt thereof, is increased by about 2 fold to about 50 fold compared to the therapeutic agent prior to performing the process.

7. The process of claim 1, wherein each of the one of more polymers is independently selected from the group consisting of a carboxylic acid functionalized polymer, a neutral non-cellulosic polymer, and a cellulosic polymer.

8. The process of claim 1, wherein the polymer is copovidone.

9. The process of claim 1, wherein the coating of step ii) further comprises one or more of (a) mixing and melting and/or softening the nanoparticle form of the pharmaceutical composition or therapeutic agent; (b) extruding the nanoparticle form of the pharmaceutical composition or therapeutic agent; and (c) cooling and/or shaping the pharmaceutical composition or therapeutic agent.

10. The process of claim 1, wherein the one or more polymers of step ii) is applied to the pharmaceutical composition as a coating of about 400 nm thickness or less.

11. The process of claim 1, wherein the one or more polymers of step ii) is applied to the pharmaceutical composition as a coating of about 400 nm thickness or greater.

12. The process of claim 1, wherein the ball milling apparatus is an attritor apparatus.

13. A continuous process, consisting of:
   i) milling a pharmaceutical composition in a ball milling apparatus to produce a milled nanoparticle form of the pharmaceutical composition; wherein the milling is performed in the absence of a solvent component; and
   ii) coating the milled nanoparticle form of the pharmaceutical composition with one or more polymers to yield a coated nanoparticle pharmaceutical composition comprising about 10% w/w to about 12% w/w polymer, wherein the coating is performed using a melt extrusion process, a melt blown process, a spunbond process, or a high temperature milling process;
   wherein the pharmaceutical composition comprises a therapeutic agent selected from dasatinib, abiraterone, raloxifene, capecitabine, methotrexate, diclofenac, and prednisone, or a pharmaceutically acceptable salt thereof, and one or more pharmaceutically acceptable excipients.

* * * * *